(12) United States Patent
Leigh et al.

(10) Patent No.: US 7,563,935 B2
(45) Date of Patent: Jul. 21, 2009

(54) CRYSTAL FORMS OF ASTAXANTHIN

(75) Inventors: Steve Leigh, Muttenz (CH); Mathew Louis Steven Leigh, Basel (CH); Peter Van Hoogevest, Bubendorf (CH)

(73) Assignee: Phares Pharmaceutical Research N.V. et al., Curacao (NL)

( * ) Notice: Subject to any disclaimer, the term of this patent is extended or adjusted under 35 U.S.C. 154(b) by 0 days.

(21) Appl. No.: 12/032,281

(22) Filed: Feb. 15, 2008

(65) Prior Publication Data

US 2008/0234521 A1    Sep. 25, 2008

Related U.S. Application Data

(63) Continuation of application No. PCT/EP2006/008047, filed on Aug. 15, 2006.

(30) Foreign Application Priority Data

Aug. 15, 2005  (EP)  ................... 05017709

(51) Int. Cl.
    C07C 45/00    (2006.01)
(52) U.S. Cl. ..................................... 568/345
(58) Field of Classification Search .................. 568/345
    See application file for complete search history.

(56) References Cited

U.S. PATENT DOCUMENTS

| | | | |
|---|---|---|---|
| 2,681,891 | A | 11/1958 | Bauernfeind et al. |
| 5,364,563 | A | 11/1994 | Cathrein et al. |
| 5,654,488 | A | 8/1997 | Krause et al. |
| 6,093,348 | A | 7/2000 | Kowalski et al. |
| 6,296,877 | B1 | 10/2001 | Auweter et al. |
| 6,406,735 | B2 | 6/2002 | Stein et al. |
| 6,827,941 | B1 | 12/2004 | Lüddecke et al. |
| 6,863,914 | B1 | 3/2005 | Auweter et al. |
| 2004/0253664 | A1 | 12/2004 | Long, II |
| 2005/0260145 | A1 | 11/2005 | Leigh et al. |
| 2005/0260154 | A1 | 11/2005 | Osslund |

FOREIGN PATENT DOCUMENTS

| | | | |
|---|---|---|---|
| EP | 0 329 754 B1 | 8/1989 |
| EP | 0 331 730 A1 | 9/1989 |
| EP | 0 733 619 A1 | 9/1996 |
| EP | 0 978 508 A2 | 2/2000 |
| JP | 7-118226 A | 5/1995 |
| JP | 11-049972 A | 2/1999 |
| WO | WO 86/06082 A1 | 10/1986 |
| WO | WO 89/01077 A1 | 2/1989 |
| WO | WO 89/01997 A1 | 3/1989 |
| WO | WO 03/102116 A2 | 12/2003 |

OTHER PUBLICATIONS

Form PCT/ISA/210 (International Search Report) dated Dec. 12, 2006.
Manuel Buchwald et al, "Optical Properties of Astaxanthin Solutions and Aggregates", Biochemistry, Feb. 1968, vol. 7, No. 2, pp. 834-843, XP-002408764 (cited in the attached International Search Report).
Hideki Hashimoto et al , "Molecular Structures of Carotenoids as Predicted by MNDO-AMI Molecular Orbital Calculations", Journal of Molecular Structure, 2002, vol. 604, No. 2-3, pp. 125-146, XP-002408765 (cited in the attached International Search Report).
Erich Widmer et al., "Technische Verfahren Zur Synthese Von Carotinoiden Und Verwandten Verbindungen Aus Oxo-Isophoron. I. Modifizierung Der *Kienzle-Mayer*-Synthese Von (3S, 3'S)-Astaxanthin" (Technical Procedures for the Synthesis of Carotenoids and Related Compounds From Oxo-Isophorone. I. Modification of the *Kienzle-Mayer*-Sysnthesis of (3S-3'S)-Astaxanthin), Helvetica Chimica Actra, vo 64, No. 237, 1981, pp. 2405-2418, XP-002408766 (cited in the attached International Search Report).
Sherry L. Morissette et al., "High-Throughput Crystallization: Polymorphs, Salts, CO-Crystals and Solvates of Pharmaceutical Solids", Advanced Drug Delivery Reviews, 2004, vol. 56, No. 3, pp. 275-300, XP-009072233 (cited in the attached International Search Report).
N. F. Haard, "Astaxanthin Formation by the Yeast *Phaffia Rhodozyma* on Molasses", Biotechnology Letters, 1988, vol. 10, No. 9, pp. 609-614 (cited on p. 18 of the specification).

*Primary Examiner*—Sikarl A Witherspoon
(74) *Attorney, Agent, or Firm*—Buchanan Ingersoll & Rooney PC

(57) ABSTRACT

Mixtures of specific crystal forms of astaxanthin and the individual crystal forms designated crystal Form I and II and disclosed together with methods for preparing said crystal Forms. Methods for preparing nutritional dosage forms including the disclosed astaxanthin crystal forms for the life science industry are also disclosed.

42 Claims, 5 Drawing Sheets

A: Spectrum of astaxanthin crystal Form I
B: Spectrum of astaxanthin crystal Form II
C: Measured spectrum of a mixture of astaxanthin crystal Form I and Form II
D: Calculated spectrum of a mixture of astaxanthin crystal Form I and Form II in a ratio of 0.55 : 0.45

CRYSTAL FORMS OF ASTAXANTHIN

RELATED APPLICATIONS

This application claims priority under 35 U.S.C. §119 to European Patent Application 05 017 709.6 filed in Europe on Aug. 15, 2005, and as a continuation application under 35 U.S.C. §120 to PCT/EP2006/008047 filed as an International Application on Aug. 15, 2006 designating the U.S., the entire contents of which are hereby incorporated by reference in their entireties.

TECHNICAL FIELD

This disclosure relates to crystal forms comprising astaxanthin and to related processes, compositions and methods.

BACKGROUND INFORMATION

Delivering a colourant such as astaxanthin with good oral bioavailability for improved plasma uptake and flesh deposition in salmonid is a particular concern for fish feed producers and fish farmers. Because of poor solubility in a physiological milieu, administration of astaxanthin crystals in fish feed pellets and other nutritional dosage forms does not give sufficient oral uptake of the colourant. In order to make the colourant more bioavailable, several methods have been developed for preparing particulate astaxanthin compositions which are dispersible in water for processing into feed pellets. The dispersible compositions are prepared by dissolving crystalline astaxanthin in solvents (U.S. Pat. No. 6,863,914 and U.S. Pat. No. 6,406,735) or oils (U.S. Pat. No. 5,364,563) under high pressure and temperature, immediately followed by dispersing the organic solution in aqueous hydrocolloid. Alternatively, the carotenoid is melted in an aqueous excipient-matrix and emulsified under pressure without using solvent or oil (U.S. Pat. No. 6,093,348). All the methods involve further processing to prepare powder formulations from the aqueous dispersions. None of the disclosures describe the type of astaxanthin crystal used in terms of their crystal structure as disclosed by X-ray diffraction and Raman spectroscopy. Despite the onerous conditions required for preparing astaxanthin compositions there has been little effort directed towards making the methods more production friendly. One way to reduce energy and solvent consumption would be to utilise different crystal forms of astaxanthin that have advantageous solubility, melting or stability characteristics, thereby allowing more gentle processing conditions. Surprisingly, the disclosures are particularly silent on specific crystal forms of astaxanthin and their potential utility for preparing astaxanthin compositions. Different crystal forms can affect in vivo dissolution rate and allow higher (supersaturated) concentrations of carotenoids in oily administration vehicles which may in turn provide higher oral uptake and bioavailability.

U.S. Pat. No. 6,827,941 describes amorphous aggregates of astaxanthin which are prepared from dilute astaxanthin solutions in acetone (50 mg/liter) followed by 20 fold dilution with water/acetone 7/3 (v/v.). It is silent regarding formation of specific crystal forms. U.S. Pat. No. 5,654,488 describes the synthesis and crystallisation of trans-astaxanthin from the reaction mixture using the Wittig process but fails to specify the crystal structure or structures that are obtained. The disclosures of the foregoing patents are incorporated herein by reference in their entireties.

SUMMARY

This disclosure relates to a mixture of novel, previously undisclosed crystal forms comprising astaxanthin herein designated crystal Form I and crystal Form II and methods for preparing said crystal forms. In addition the disclosure describes crystal Form I and crystal Form II and combinations thereof comprising defined amounts of all-trans-astaxanthin with different amounts of (other) carotenoidal compounds. It further covers administration forms comprising crystal Form I or Form II or combinations thereof and the use of either crystal Form 1 or crystal Form II or combinations thereof dissolved or suspended in oil or organo-solvent. The solutions or dispersions may be used to prepare solid compositions comprising astaxanthin in hydrophilic or lipophilic dispersant carriers or may be used to prepare physical forms of astaxanthin.

A mixture containing (e.g., consisting essentially of crystal forms of astaxanthin is disclosed comprising a) Crystal Form I characterized by at least one of i) The X-ray diffraction pattern comprising the following interlattice plane interval d in $10^{-10}$ m: 8.0±0.1, 6.5±0.05, 6.3±0.05, 6.1±0.05, 5.96±0.05, 5.58±0.05, 5.43±0.05, 4.87±0.05, 4.32±0.05, 4.24±0.05, 4.21±0.05, 4.07±0.05, 4.03±0.05, 3.58±0.05, 3.50 ±0.05, ii) the Raman spectrum containing peaks at; 372±2, 346±2, 333±2, 312±2, 289±2, 234±2, 193±2, 178±2, 133±2, 82±2, $cm^{-1}$; and, optionally, at least one of, iii) a DSC scan showing a phase transition at 212-222° C.; and iv) a solubility profile in dichloromethane of 35-45 g/l at 20° C.-25° C.; and b) Crystal Form II characterized by at least one of the X-ray diffraction pattern comprising the following interlattice plane interval d in $10^{-10}$ m: 7.2±0.1, 6.6±0.05, 6.5±0.05, 5.48±0.05, 5.34±0.05, 5.27±0.05, 4.49±0.05, 4.38±0.05, 4.12±0.05, 3.89±0.05, 3.61±0.05, 3.56±0.05, 3.34±0.05, 3.32±0.05, 3.22±0.05; and ii) the Raman spectrum containing peaks at 376±2, 337±2, 314±2, 304±2, 289±2, 206±2, 180±2, 137±2, 107±2, 93±2, $cm^{-1}$; and, optionally, at least one of iii) A DSC scan showing a phase transition at 225-240° C.; and iv) a solubility profile in dichloromethane of 10-30 g/l at 20° C.-25° C.

A composition comprising a crystalline form of astaxanthin designated crystal Form I is disclosed characterized by at least one of i) The X-ray diffraction pattern comprising the following interlattice plane interval d in $10^{-10}$ m: 8.0±0.1, 6.5 ±0.05, 6.3±0.05, 6.1±0.05, 5.96±0.05, 5.58±0.05, 5.43±0.05, 4.87±0.05, 4.32±0.05, 4.24±0.05, 4.21±0.05, 4.07±0.05, 4.03±0.05, 3.58±0.05, 3.50±0.05, ii) the Raman spectrum containing peaks at; 372±2, 346±2, 333±2, 312±2, 289±2, 234±2, 193±2, 178±2, 133±2, 82±2, $cm^{-1}$; and, optionally, at least one of, iii) a DSC scan showing a phase transition at 212-222° C.; and iv) a solubility profile in dichloromethane of 35-45 g/l at 20° C.-25° C.

A composition comprising a crystalline form of astaxanthin designated crystal Form II is disclosed characterized by at least one of i) the X-ray diffraction pattern comprising the following interlattice plane interval d in $10^{-10}$ m: 7.2±0.1, 6.6±0.05, 6.5±0.05, 5.48±0.05, 5.34±0.05, 5.27±0.05, 4.49±0.05, 4.38±0.05, 4.12±0.05, 3.89±0.05, 3.61±0.05, 3.56±0.05, 3.34±0.05, 3.32±0.05, 3.22±0.05; and ii) the Raman spectrum containing peaks at a Raman spectrum containing peaks at 376±2, 337±2, 314±2, 304±2, 289±2, 206±2, 180±2, 137±2, 107±2, 93±2, $cm^{-1}$; and, optionally, at least one of iii) a DSC scan showing a phase transition at 225-240° C.; and iv) a solubility profile in dichloromethane of 10-30 g/l at 20° C.-25° C.

A crystalline form of astaxanthin designated crystal Form I is disclosed characterized by at least one of i) the X-ray diffraction pattern comprising the following interlattice plane interval d in $10^{-10}$ m: 8.0±0.1, 6.5±0.05, 6.3±0.05, 6.1±0.05, 5.96±0.05, 5.58±0.05, 5.43±0.05, 4.87±0.05, 4.32±0.05, 4.24±0.05, 4.21±0.05, 4.07±0.05, 4.03±0.05, 3.58±0.05, 3.50±0.05, ii) the Raman spectrum containing peaks at; 372±2, 346±2, 333±2, 312±2, 289±2, 234±2, 193±2, 178±2, 133±2, 82±2, cm$^{-1}$; and, optionally, at least one of, vii) a DSC scan showing a phase transition at 212-222° C.; and viii) a solubility profile in dichloromethane of 35-45 g/l at 20° C.-25° C.

A crystalline form of astaxanthin designated crystal Form I is disclosed providing an X-ray powder diffraction pattern substantially in agreement with the X-ray powder diffraction pattern provided in FIG. 1.

A crystalline form of astaxanthin designated crystal Form I is disclosed providing a Raman spectrum substantially in agreement with the Raman spectrum provided in FIG. 2.

A crystalline form of astaxanthin designated crystal Form II is disclosed characterized by at least one of i) the X-ray diffraction pattern comprising the following interlattice plane intervals d in $10^{-10}$ m: 7.2±0.1, 6.6±0.05, 6.5±0.05, 5.48±0.05, 5.34±0.05, 5.27±0.05, 4.49±0.05, 4.38±0.05, 4.12±0.05, 3.89±0.05, 3.61±0.05, 3.56±0.05, 3.34±0.05, 3.32±0.05, 3.22±0.05; and ii) the Raman spectrum containing peaks at 376±2, 337±2, 314±2, 304±2, 289±2, 206±2, 180±2, 137±2, 107±2, 93±2, cm$^{-1}$; and, optionally, at least one of iii) a DSC scan showing a phase transition at 225-240° C.; and iv) a solubility profile in dichloromethane of 10-30 g/l at 20° C.-25° C.

A crystalline form of astaxanthin designated crystal Form II is disclosed providing an X-ray powder diffraction pattern substantially in agreement with the X-ray powder diffraction pattern provided in FIG. 3.

A crystalline form of astaxanthin designated crystal Form II is disclosed providing a Raman spectrum substantially in agreement with the Raman spectrum provided in FIG. 4.

A process for preparing a crystalline form of astaxanthin designated crystal Form I is disclosed or a mixture of crystal Form I and crystal Form II is disclosed which comprises a crystallization process comprising (e.g., consisting of) i) dissolving astaxanthin, comprising all-trans-astaxanthin and maximally 7 mol % of at least one carotenoidal compound, selected from the group consisting of at least one 9-cis-astaxanthin, 13-cis-astaxanthin, 15-cis-astaxanthin, astacene, semi-astacene and C-25 aldehyde in a solvent, selected from the group consisting of dichloromethane, trichloroethane, chloroform, dimethoxymethane, diethoxyethane, dioxacyclopentane, THF, NMP, N-ethylpyrrolidone, toluene, pyridine and carbon disulfide, ii) subjecting the solution to at least one treatment selected from the group consisting of heat, light, oxidizing agents and further steps selected from the group consisting of, iiia) addition of an anti-solvent, iiib) removal of the solvent by evaporation or optionally by simultaneous exchange of the solvent with an anti solvent, iii) cooling the organic solvent solution with or without the addition of a nucleating agent or seed and iv) harvesting, washing with an anti solvent and drying the crystals.

DETAILED DESCRIPTION

In this disclosure the following definitions apply:

"Astaxanthin" comprises all-trans-astaxanthin (3,3'-dihydroxy-β,β-carotene-4,4'-dione) together with not more than 25% by weight of other carotenoidal compounds (including the cis isomers of astaxanthin).

"Carotenoidal compounds" include astaxanthin metabolites, synthetic or natural astaxanthin derivatives e.g. etherified or esterified, oxidation or hydrogenation products and cis isomers. The term includes by-products obtained during synthesis and crystallization of astaxanthin or during the extraction process of the astaxanthin from natural sources. Typical astaxanthin related carotenoidal compounds are e.g. 9-cis-astaxanthin, 13-cis-astaxanthin, 15-cis-astaxanthin, astacene, semi-astacene and the C-25 aldehyde (all-trans-3-hydroxy-4-oxo-12'-apo-beta-caroten-12'-al, with CAS Nr. 72523-68-3). The term specifically excludes all -trans-astaxanthin. The term covers the "total carotenoids other than astaxanthin" requirement in the US-FDA specifications for astaxanthin as described in 21 CFR 73.35.

"Mol %" indicates the purity of a crystal Form with respect to total molar carotenoid content, which is the sum of all-trans-astaxanthin and carotenoidal compounds.

Figure 1:
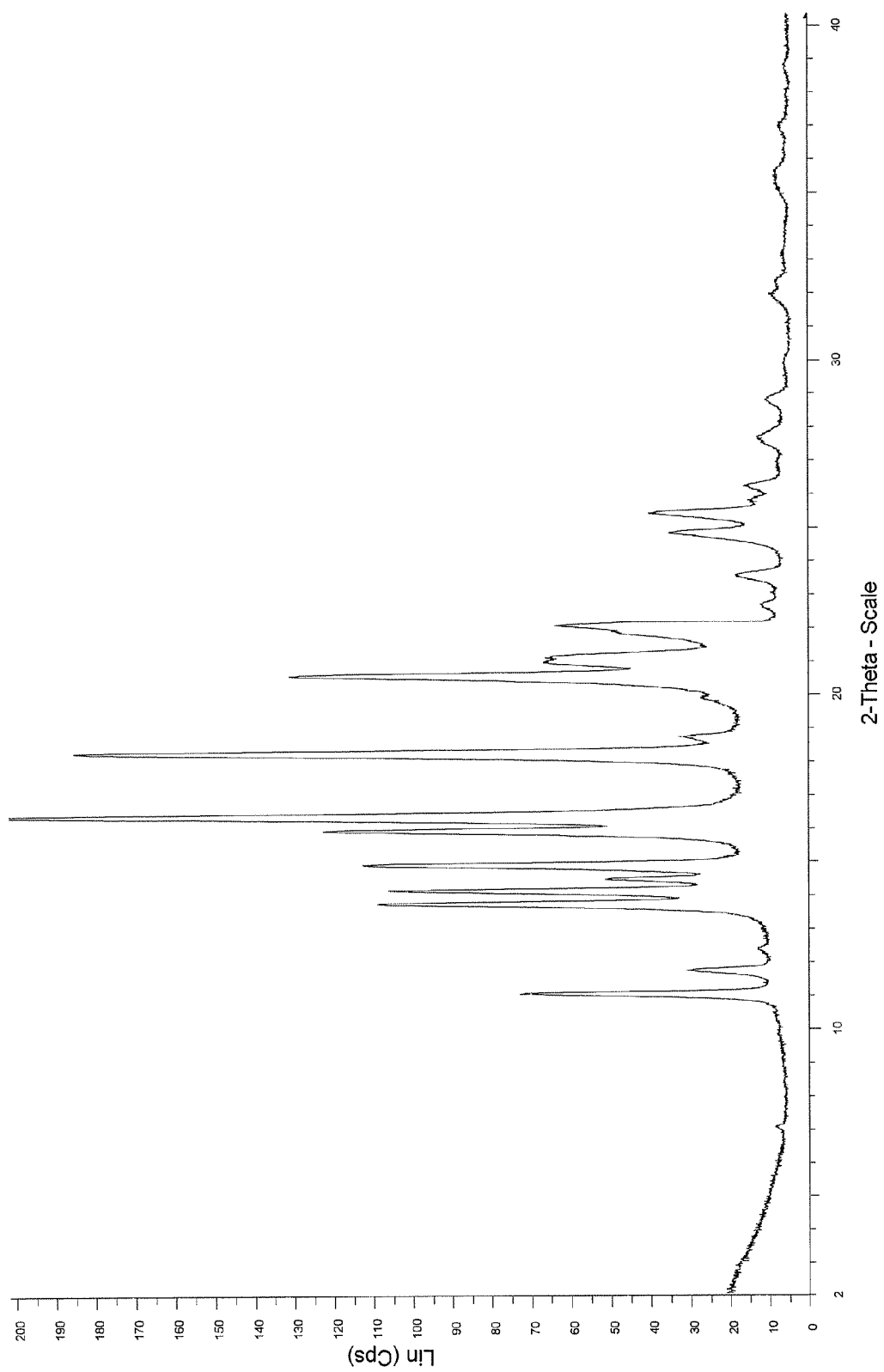
FIG. 1 shows an exemplary X-ray diffractogram of crystal Form I of astaxanthin.
Figure 2:
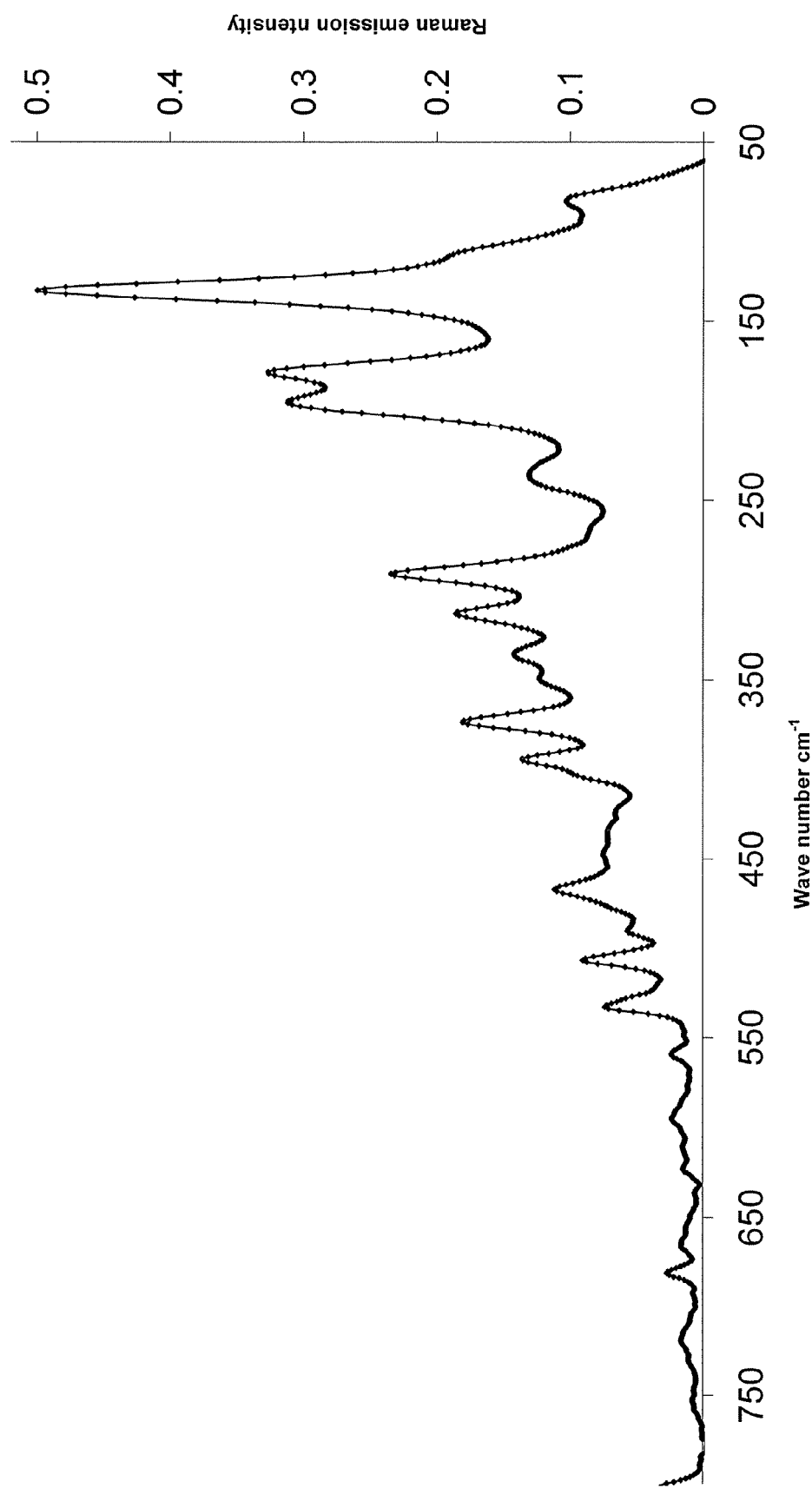
FIG. 2 shows an exemplary Raman spectrum of crystal Form I of astaxanthin.
Figure 3:
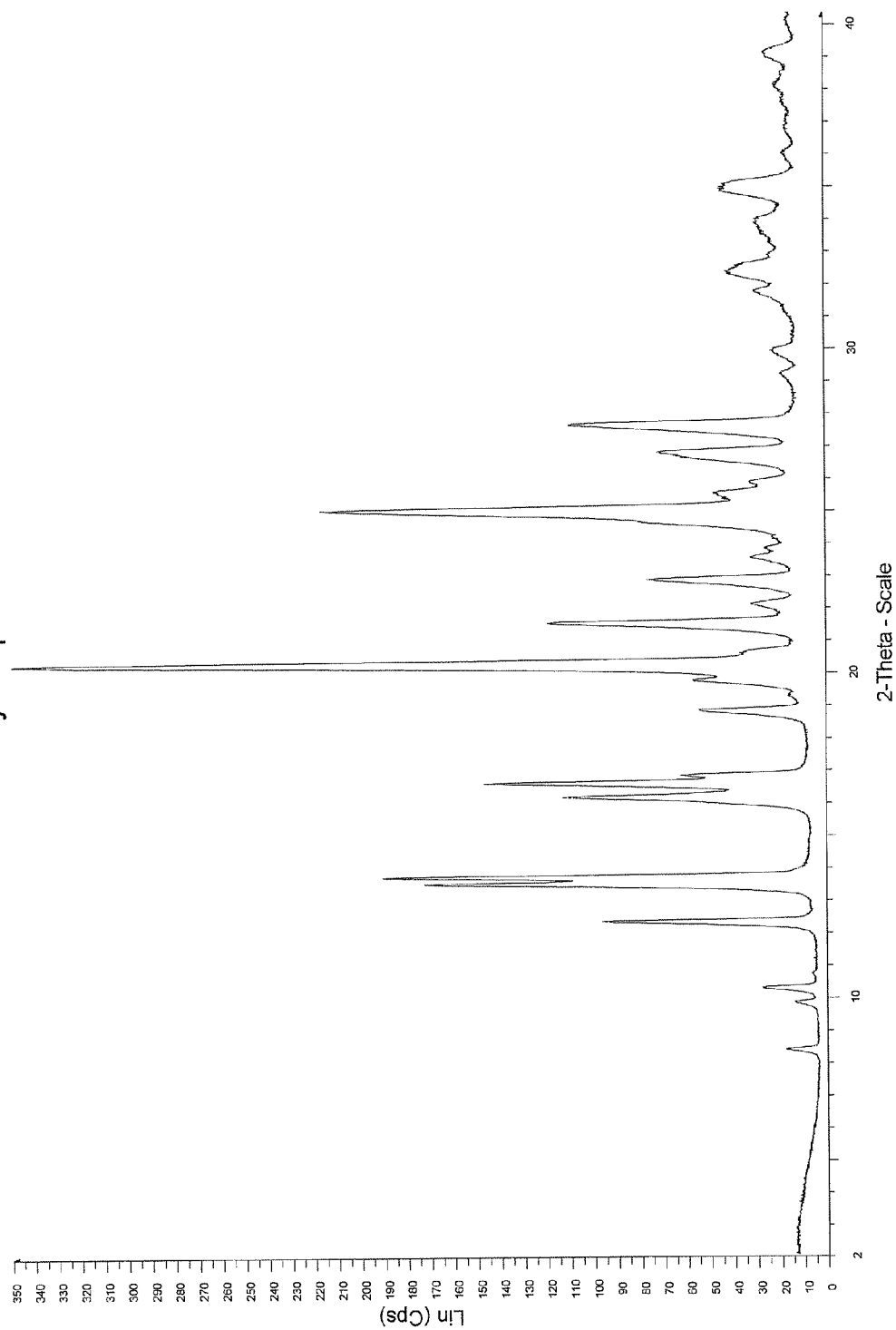
FIG. 3 shows an exemplary X-ray diffractogram of crystal Form II of astaxanthin.
Figure 4:
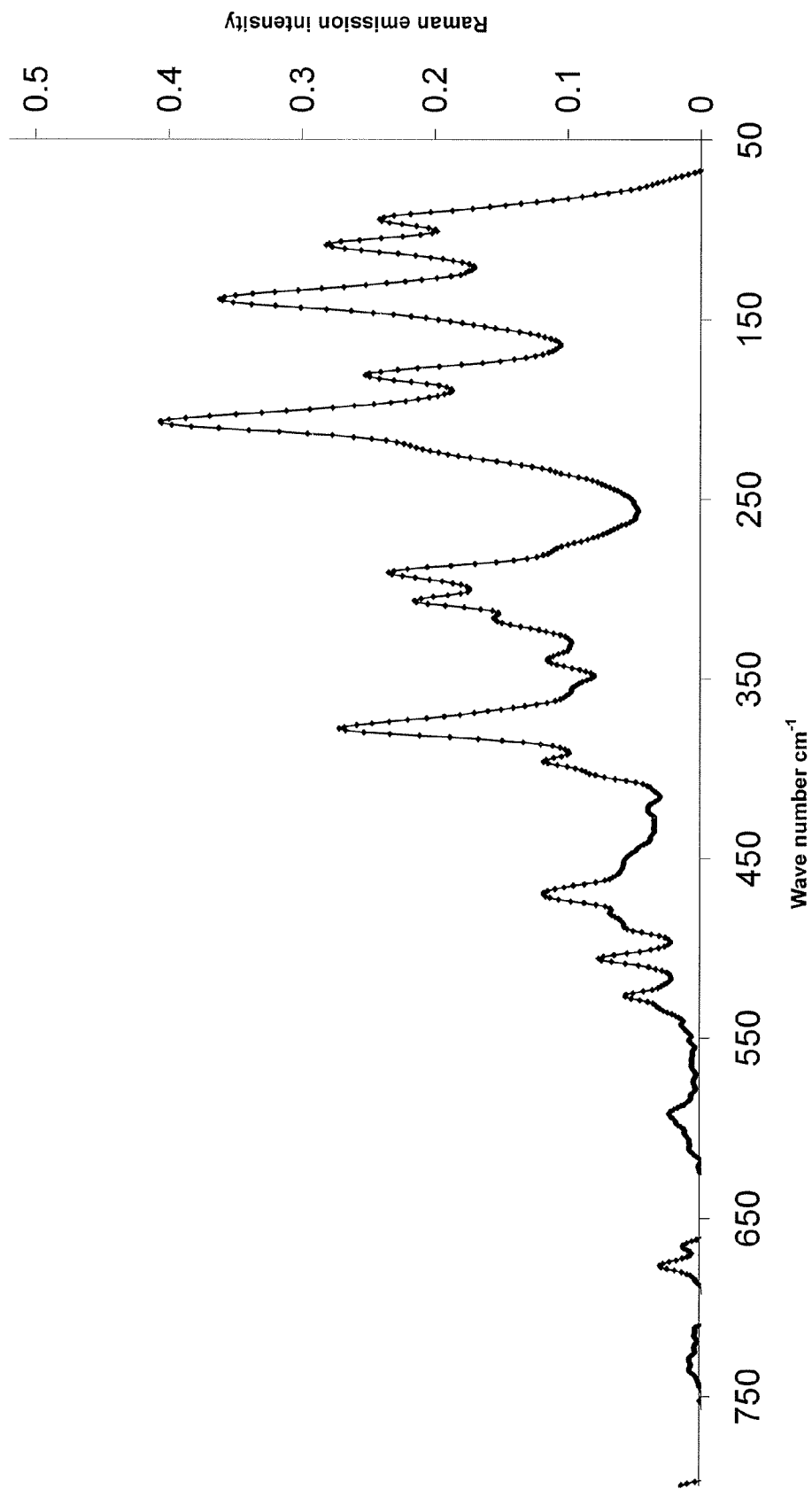
FIG. 4 shows an exemplary Raman spectrum of crystal Form II of astaxanthin.

"Substantially in agreement" with an X-ray powder diffraction or Raman spectrum provided in the figure means that any spectrum exhibiting the same sequence of peaks and minima, showing the same ratio of intensity of said peaks and minima at the same wave number (Raman) and Theta and d interlattice interval position (X-ray) within a standard deviation of ±5% complies with the characteristic X-Ray and Raman spectra for astaxanthin Crystal Form I shown in FIG. 1 and FIG. 2, respectively, or the X-Ray and Raman spectra for crystal Form II shown in FIG. 3 and FIG. 4 respectively.

"About" refers to a standard deviation of 20% on either side of the limits in mol % of carotenoidal compounds in the solution for preparing crystal Form I or Form II or mixtures thereof, or in said crystal Forms.

"Lipophilic dispersing agent" is a solid substance with water solubility at room temperature lower than or equal to 5 mg/ml which has the property to embed a molecular or colloidal dispersion or aggregates of the astaxanthin in a solid composition.

"Hydrophilic dispersing agent" is a solid substance with water solubility at room temperature higher than 5 mg/ml which has the property to act as a wetting agent to enhance the suspension of astaxanthin in an aqueous phase. The definition also refers to o/w emulsifiers, polymers and hydrocolloids.

"Solid composition" means that the astaxanthin is distributed in a solid matrix which is prepared by dissolving the carotenoid and the lipophilic or hydrophilic dispersing agent together in a mutual solvent or combination of solvents, followed by removal of the solvent or solvent mixture.

"Water miscible solvent" means that the solvent can be mixed in any ratio with water without phase separation, e.g. ethanol.

"Water immiscible solvent" means that the solvent can be mixed only partially with water without phase separation, e.g. dichloromethane.

"Anti-solvent" is a crystallisation liquid which is miscible with the solvent in which the all-trans-astaxanthin and carotenoidal compounds are dissolved but has a lower solvency or practically no solvent properties (for astaxanthin) at the temperature that causes crystallisation of the specific crystal form. The definition includes water. By definition, astaxanthin has a solubility of less than 1 mg/ml in the anti-solvent at room temperature or below, e.g. methanol.

"Life science industry" includes food, feed, pharmaceutical, aquaculture, cosmetic, nutriceutical, veterinary industries.

The disclosure is in the area of "crystal forms" and "colourant compositions" comprising natural or synthetic astaxanthin.

The disclosure describes the following embodiments:

A mixture comprising (e.g., consisting essentially of) crystal forms of astaxanthin comprising
  a) Crystal Form I characterized by at least one of
    i) The X-ray diffraction pattern comprising the following interlattice plane interval d in $10^{-10}$ m: 8.0±0.1, 6.5±0.05, 6.3±0.05, 6.1±0.05, 5.96±0.05, 5.58±0.05, 5.43±0.05, 4.87±0.05, 4.32±0.05, 4.24±0.05, 4.21±0.05, 4.07±0.05, 4.03±0.05, 3.58±0.05, 3.50±0.05,
    ii) The Raman spectrum containing peaks at; 372±2, 346±2, 333±2, 312±2, 289±2, 234±2, 193±2, 178±2, 133±2, 82±2, $cm^{-1}$; and, optionally, at least one of,
    iii) A DSC scan showing a phase transition at 212-222° C.; and
    iv) A solubility profile in dichloromethane of 35-45 g/l at 20° C.-25° C.; and
  b) Crystal Form II characterized by at least one of
    i) The X-ray diffraction pattern comprising the following interlattice plane interval d in $10^{-10}$ m: 7.2±0.1, 6.6±0.05, 6.5±0.05, 5.48±0.05, 5.34±0.05, 5.27±0.05, 4.49±0.05, 4.38±0.05, 4.12±0.05, 3.89±0.05, 3.61±0.05, 3.56±0.05, 3.34±0.05, 3.32±0.05, 3.22±0.05; and
    ii) The Raman spectrum containing peaks at 376±2, 337±2, 314±2, 304±2, 289±2, 206±2, 180±2, 137±2, 107±2, 93±2, $cm^{-1}$; and, optionally, at least one of
    iii) A DSC scan showing a phase transition at 225-240° C.; and
    iv) A solubility profile in dichloromethane of 10-30 g/l at 20° C.-25° C.

An exemplary preferred embodiment relates to a mixture comprising (e.g., consisting essentially of):
  20% to 80% by weight of the crystalline form of astaxanthin designated crystal Form I; and
  80% to 20% by weight of the crystalline form of astaxanthin designated crystal Form II.

An exemplary preferred embodiment relates to a mixture comprising (e.g., consisting essentially of):
  10% to 90% by weight of the crystalline form of astaxanthin designated crystal Form I; and
  90% to 10% by weight of the crystalline form of astaxanthin designated crystal Form II.

An exemplary preferred embodiment relates to a mixture comprising (e.g., consisting essentially of):
  95% to 5% by weight of the crystalline form of astaxanthin designated crystal Form I; and
  5% to 95% by weight of the crystalline form of astaxanthin designated crystal Form II.

An exemplary preferred embodiment relates to a mixture comprising (e.g., consisting essentially of):
  99.9% to 0.1% by weight of the crystalline form of astaxanthin designated crystal Form I; and
  0.1% to 99.9% by weight of the crystalline form of astaxanthin designated crystal Form II.

A further exemplary embodiment relates to a composition comprising a crystalline form of astaxanthin designated crystal Form I characterized by at least one of:
  i) The X-ray diffraction pattern comprising the following interlattice plane interval d in $10^{-10}$ m: 8.0±0.1, 6.5±0.05, 6.3±0.05, 6.1±0.05, 5.96±0.05, 5.58±0.05, 5.43±0.05, 4.87±0.05, 4.32±0.05, 4.24±0.05, 4.21±0.05, 4.07±0.05, 4.03±0.05, 3.58±0.05, 3.50±0.05,
  ii) The Raman spectrum containing peaks at; 372±2, 346±2, 333±2, 312±2, 289±2, 234±2, 193±2, 178±2, 133±2, 82±2, $cm^{-1}$; and, optionally, at least one of,
  iii) A DSC scan showing a phase transition at 212-222° C.; and
  iv) A solubility profile in dichloromethane of 35-45 g/l at 20° C.-25° C.

Another exemplary embodiment relates to a composition comprising a crystalline form of astaxanthin designated crystal Form II characterized by at least one of:
  i) The X-ray diffraction pattern comprising the following interlattice plane interval d in $10^{-10}$ m: 7.2±0.1, 6.6±0.05, 6.5±0.05, 5.48±0.05, 5.34±0.05, 5.27±0.05, 4.49±0.05, 4.38±0.05, 4.12±0.05, 3.89±0.05, 3.61±0.05, 3.56±0.05, 3.34±0.05, 3.32±0.05, 3.22±0.05; and
  ii) The Raman spectrum containing peaks at a Raman spectrum containing peaks at 376±2, 337±2, 314±2, 304±2, 289±2, 206±2, 180±2, 137±2, 107±2, 93±2, $cm^{-1}$; and, optionally, at least one of
  iii) A DSC scan showing a phase transition at 225-240° C.; and
  iv) A solubility profile in dichloromethane of 10-30 g/l at 20° C.-25° C.

Additional subject matter of the present disclosure is a process for preparing the above-mentioned composition, which comprises adding excipients to crystal Form I and a process, which comprises adding excipients to crystal Form II.

An exemplary preferred embodiment relates to a crystalline form of astaxanthin designated crystal Form I characterized by at least one of:
  i) The X-ray diffraction pattern comprising the following interlattice plane interval d in $10^{-10}$ m: 8.0±0.1, 6.5±0.05, 6.3±0.05, 6.1±0.05, 5.96±0.05, 5.58±0.05, 5.43±0.05, 4.87±0.05, 4.32±0.05, 4.24±0.05, 4.21±0.05, 4.07±0.05, 4.03±0.05, 3.58±0.05, 3.50±0.05,
  ii) The Raman spectrum containing peaks at; 372±2, 346±2, 333±2, 312±2, 289±2, 234±2, 193±2, 178±2, 133±2, 82±2, $cm^{-1}$; and, optionally, at least one of,
  iii) A DSC scan showing a phase transition at 212-222° C.; and
  iv) A solubility profile in dichloromethane of 35-45 g/l at 20° C.-25° C.

An exemplary preferred embodiment relates to the crystalline form of astaxanthin designated crystal Form I providing an X-ray powder diffraction pattern substantially in agreement with the X-ray powder diffraction spectrum provided in FIG. 1.

An exemplary preferred embodiment relates to a crystalline form of astaxanthin designated crystal Form I providing a Raman spectrum substantially in agreement with the Raman spectrum provided in FIG. 2.

A further exemplary preferred embodiment relates to a crystalline form of astaxanthin designated crystal Form I characterized by at least one of:
i) The X-ray diffraction pattern comprising the following interlattice plane interval d in $10^{-10}$ m: 8.0±0.1, 6.5±0.05, 6.3±0.05, 6.1±0.05, 5.96±0.05, 5.58±0.05, 5.43±0.05, 4.87±0.05, 4.32±0.05, 4.24±0.05, 4.21±0.05, 4.07±0.05, 4.03±0.05, 3.58±0.05, 3.50±0.05,
ii) The Raman spectrum containing peaks at; 372±2, 346±2, 333±2, 312±2, 289±2, 234±2, 193±2, 178±2, 133±2, 82±2, $cm^{-1}$; and, optionally, at least one of,
v) A DSC scan showing a phase transition at 212-222° C.; and
vi) A solubility profile in dichloromethane of 35-45 g/l at 20° C.-25° C. and comprising all-trans-astaxanthin and at least about 13 mol % of at least one carotenoidal compound.

A further exemplary preferred embodiment relates to the crystalline form of astaxanthin designated crystal Form I characterized by at least one of:
i) The X-ray diffraction pattern comprising the following interlattice plane interval d in $10^{-10}$ m: 8.0±0.1, 6.5±0.05, 6.3±0.05, 6.1±0.05, 5.96±0.05, 5.58±0.05, 5.43±0.05, 4.87±0.05, 4.32±0.05, 4.24±0.05, 4.21±0.05, 4.07±0.05, 4.03±0.05, 3.58±0.05, 3.50±0.05,
ii) The Raman spectrum containing peaks at; 372±2, 346±2, 333±2, 312±2, 289±2, 234±2, 193±2, 178±2, 133±2, 82±2, $cm^{-1}$; and, optionally, at least one of,
iii) A DSC scan showing a phase transition at 212-222° C.; and
iv) A solubility profile in dichloromethane of 35-45 g/l at 20° C.-25° C. and comprising all-trans-astaxanthin and at least about 13 mol % of at least one carotenoidal compound, selected from the group consisting of 9-cis-astaxanthin, 13-cis-astaxanthin, 15-cis-astaxanthin, astacene, semi-astacene and C-25 aldehyde.

Another exemplary preferred embodiment relates to a crystalline form of astaxanthin designated crystal Form II characterized by at least one of:
i) The X-ray diffraction pattern comprising the following interlattice plane intervals d in $10^{-10}$ m: 7.2±0.1, 6.6±0.05, 6.5±0.05, 5.48±0.05, 5.34±0.05, 5.27±0.05, 4.49±0.05, 4.38±0.05, 4.12±0.05, 3.89±0.05, 3.61±0.05, 3.56±0.05, 3.34±0.05, 3.32±0.05, 3.22±0.05; and
ii) The Raman spectrum containing peaks at 376±2, 337±2, 314±2, 304±2, 289±2, 206±2, 180±2, 137±2, 107±2, 93±2, $cm^{-1}$; and, optionally, at least one of
iii) A DSC scan showing a phase transition at 225-240° C.; and
iv) A solubility profile in dichloromethane of 10-30 g/l at 20° C.-25° C.

An exemplary preferred embodiment relates to the crystalline form of astaxanthin designated crystal Form II providing an X-ray powder diffraction pattern substantially in agreement with the X-ray powder diffraction spectrum provided in FIG. 3.

An exemplary preferred embodiment relates to a crystalline form of astaxanthin designated crystal Form II providing the Raman spectrum substantially in agreement with a Raman spectrum provided in FIG. 4.

Another exemplary preferred embodiment relates to a crystalline form of astaxanthin designated crystal Form II characterized by at least one of
i) The X-ray diffraction pattern comprising the following interlattice plane interval d in $10^{-1}$ m: 7.2±0.1, 6.6±0.05, 6.5±0.05, 5.48±0.05, 5.34±0.05, 5.27±0.05, 4.49±0.05, 4.38±0.05, 4.12±0.05, 3.89±0.05, 3.61±0.05, 3.56±0.05, 3.34±0.05, 3.32±0.05, 3.22±0.05; and
ii) The Raman spectrum containing peaks at 376±2, 337±2, 314±2, 304±2, 289±2, 206±2, 180±2, 137±2, 107±2, 93±2, $cm^{-1}$; and, optionally, at least one of
iii) A DSC scan showing a phase transition at 225-240° C.; and
iv) A solubility profile in dichloromethane of 10-30 g/l at 20° C.-25° C. and comprising all-trans-astaxanthin and maximally about 7 mol % of at least one carotenoidal compound.

Another exemplary preferred embodiment relates to a crystalline form of astaxanthin designated crystal Form II characterized by at least one of:
i) The X-ray diffraction pattern comprising the following interlattice plane interval d in $10^{-10}$ m: 7.2±0.1, 6.6±0.05, 6.5±0.05, 5.48±0.05, 5.34±0.05, 5.27±0.05, 4.49±0.05, 4.38±0.05, 4.12±0.05, 3.89±0.05, 3.61±0.05, 3.56±0.05, 3.34±0.05, 3.32±0.05, 3.22±0.05; and
ii) The Raman spectrum containing peaks at 376±2, 337±2, 314±2, 304±2, 289±2, 206±2, 180±2, 137±2, 107±2, 93±2, $cm^{-1}$; and, optionally, at least one of
iii) A DSC scan showing a phase transition at 225-240° C.; and
iv) A solubility profile in dichloromethane of 10-30 g/l at 20° C.-25° C. and comprising all-trans-astaxanthin and maximally about 7 mol % of at least one carotenoidal compound, selected from the group consisting of at least one 9-cis-astaxanthin, 13-cis-astaxanthin, 15-cis-astaxanthin, astacene, semi-astacene and C-25 aldehyde.

Another exemplary preferred embodiment relates to a crystalline form of astaxanthin designated crystal Form II characterized by at least one of:
i) The X-ray diffraction pattern comprising the following interlattice plane interval d in $10^{-10}$ m: 7.2±0.1, 6.6±0.05, 6.5±0.05, 5.48±0.05, 5.34±0.05, 5.27±0.05, 4.49±0.05, 4.38±0.05, 4.12±0.05, 3.89±0.05, 3.61±0.05, 3.56±0.05, 3.34±0.05, 3.32±0.05, 3.22±0.05; and
ii) The Raman spectrum containing peaks at 376±2, 337±2, 314±2, 304±2, 289±2, 206±2, 180±2, 137±2, 107±2, 93±2, $cm^{-1}$; and, optionally, at least one of
iii) A DSC scan showing a phase transition at 225-240° C.; and
iv) A solubility profile in dichloromethane of 10-30 g/l at 20° C.-25° C. wherein the astaxanthin complies with the following specifications as stated in 21 CFR 73.35 of the US-FDA shown in Table 1:

TABLE 1

| Quality Criteria | Specification |
|---|---|
| Physical State | Solid |
| 0.05% Solution in Chloroform | Complete and Clear |
| Absorption Maximum Wavelength | 484-493 nm (solution in chloroform) |
| Residue on Ignition | Not more than 0.1% |
| Total Carotenoid Content other than Astaxanthin | Not more than 4% |
| Lead | Not more than 5 ppm |

TABLE 1-continued

| Quality Criteria | Specification |
| --- | --- |
| Arsenic | Not more than 2 ppm |
| Mercury | Not more than 1 ppm |
| Heavy Metals | Not more than 10 ppm |
| Assay | Minimum 96% |

A further embodiment relates to a process for preparing a mixture of crystalline forms of astaxanthin designated crystal Form I and crystal Form II, comprising at least 5% w/w of Form I or Form II which comprises:
  i) dissolving a mixture of astaxanthin that comprises all-trans-astaxanthin and about 7 mol % to about 17 mol % of at least one carotenoidal compound, selected from the group consisting of at least one 9-cis-astaxanthin, 13-cis-astaxanthin, 15-cis-astaxanthin, astacene, semi-astacene and C-25 aldehyde in a solvent in which the solubility of astaxanthin is at least 1 mg/ml at a temperature up to the boiling point of said solvent and further steps selected from the group consisting of, iia) addition of an anti-solvent, iib) removal of the solvent by evaporation, optionally by simultaneous exchange of the solvent with an anti solvent, iic) cooling the organic solvent solution optionally with a nucleating agent or seed comprising crystal Form I or II, or mixtures thereof and iii) harvesting, washing with an anti solvent and drying the crystals.

A further embodiment relates to a process for preparing a crystalline form of astaxanthin designated crystal Form I, which comprises:
  i) dissolving a mixture of astaxanthin that comprises all-trans-astaxanthin and at least about 13 mol % of at least one carotenoidal compound, selected from the group consisting of at least 9-cis-astaxanthin, 13-cis-astaxanthin, 15-cis -astaxanthin, astacene, semi-astacene and C-25 aldehyde dissolved in a solvent in which the solubility of astaxanthin is at least 1 mg/ml at a temperature up to the boiling point of said solvent and further steps selected from the group consisting of, iia) addition of an anti-solvent, iib) removal of the solvent by evaporation optionally by simultaneous exchange of the solvent with an anti solvent, iic) cooling the organic solvent solution optionally with a nucleating agent or seed comprising crystal Form I and iii) harvesting, washing with an anti solvent and drying the crystals.

A further embodiment relates to a process for preparing a crystalline form of astaxanthin designated crystal Form I, which comprises:
  i) dissolving a mixture of astaxanthin that comprises all-trans-astaxanthin and at least about 13 mol % of at least one carotenoidal compound, selected from the group consisting of at least one 9-cis-astaxanthin, 13-cis-astaxanthin, 15-cis -astaxanthin, astacene, semi-astacene and C-25 aldehyde in a solvent selected from the group consisting of dichloromethane, trichloroethane, chloroform, dimethoxymethane, diethoxyethane, dioxacyclopentane, THF, NMP, N-ethylpyrrolidone, toluene, pyridine and carbon disulfide, at a temperature up to the boiling point of said solvent and further steps selected from the group consisting of, iia) addition of an anti-solvent, selected from the group consisting of methanol, ethanol, n-propanol, isopropanol, n-butanol, tert-butanol and water, iib) removal of the solvent by evaporation optionally by simultaneous exchange of the solvent with an anti solvent, iic) cooling the organic solvent solution with the optional addition of a nucleating agent or seed comprising crystal Form I and iii) harvesting, washing with an anti solvent and drying the crystals.

A further embodiment relates to a process for preparing a crystalline form of astaxanthin designated crystal Form II, which comprises:
  i) dissolving a mixture of astaxanthin that comprises all-trans-astaxanthin and essentially a maximum of about 7 mol % of at least one carotenoidal compound, selected from the group consisting of at least 9-cis-astaxanthin, 13-cis-astaxanthin, 15-cis-astaxanthin, astacene, semi-astacene and C-25 aldehyde in a solvent in which the solubility of astaxanthin is at least 1 mg/ml at a temperature up to the boiling point of said solvent and further steps selected from the group consisting of, iia) addition of an anti-solvent, iib) removal of the solvent by evaporation optionally by simultaneous exchange of the solvent with an anti solvent, iic) cooling the organic solvent solution with the optional addition of a nucleating agent or seed comprising crystal Form I and iii) harvesting, washing with an anti solvent and drying the crystals.

A further embodiment relates to a process for preparing a crystalline form of astaxanthin designated crystal Form II comprising
  i) dissolving astaxanthin, comprising all-trans-astaxanthin and essentially a maximum of about 7 mol % of at least one carotenoidal compound selected from the group consisting of at least one 9-cis-astaxanthin, 13-cis-astaxanthin, 15-cis-astaxanthin, astacene, semi-astacene and C-25 aldehyde in a solvent, selected from the group consisting of dichloromethane, trichloroethane, chloroform, dimethoxymethane, diethoxyethane, dioxacyclopentane, THF, NMP, N-ethylpyrrolidone, toluene, pyridine and carbon disulfide and further steps selected from the group consisting of, iia) addition of an anti-solvent, iib) removal of the solvent by evaporation or optionally by simultaneous exchange of the solvent with an anti solvent, iic) cooling the organic solvent solution optionally with addition of a nucleating agent or seed comprising crystal Form II and, iii) harvesting, washing with an anti solvent and drying the crystals.

A further embodiment relates to a process for preparing a crystalline form of astaxanthin designated crystal Form I or a mixture of crystal Form I and crystal Form II which comprises a crystallization process comprising (e.g., consisting of) i) dissolving astaxanthin, comprising all-trans-astaxanthin and maximally about 7 mol % of at least one carotenoidal compound, selected from the group consisting of at least one 9-cis-astaxanthin, 13-cis-astaxanthin, 15-cis-astaxanthin, astacene, semi-astacene and C-25 aldehyde in a solvent, selected from the group consisting of dichloromethane, trichloroethane, chloroform, dimethoxymethane, diethoxyethane, dioxacyclopentane, THF, NMP, N-ethylpyrrolidone, toluene, pyridine and carbon disulfide, ii) subjecting the solution to at least one treatment selected from the group consisting of heat, light, oxidizing agents and further steps selected from the group consisting of iiia) addition of an anti-solvent, iiib) removal of the solvent by evaporation or optionally by simultaneous exchange of the solvent with an anti solvent, iiic) cooling the organic solvent solution with or without the addition of a nucleating agent or seed and iv) harvesting, washing with an anti solvent and drying the crystals.

An exemplary preferred embodiment of the disclosure relates to a process which comprises further processing crystal Forms I and II or mixtures thereof defined above to nutritional dosage forms.

Another embodiment is an administration form comprising astaxanthin, crystal Form I or II, or mixtures thereof for use in the life science industry.

Another embodiment is an administration form comprising astaxanthin crystal Form I or II of astaxanthin, or mixtures thereof for use in the fish feed industry in which the content of astaxanthin is below 20% by weight.

Another embodiment is an administration form comprising a suspension of astaxanthin crystal Form I or II, or mixtures thereof in an edible oil for preparing fish feed and for use in the life science industry.

Another embodiment is a process to prepare an administration form comprising astaxanthin for use in fish feed and the life science industry wherein astaxanthin crystal Form I, or II or mixtures thereof is dissolved in an organic solvent or oil or mixtures thereof followed by further processing into said administration form.

Another embodiment is a process to prepare an administration form comprising astaxanthin for use in the life science industry wherein astaxanthin crystal Form I, or II or mixtures thereof is dissolved in an organic solvent or oil or mixtures thereof followed by further processing into said administration form which comprises a lipophilic dispersant.

Another embodiment is a process to prepare an administration form comprising astaxanthin for use in the life science industry wherein astaxanthin crystal Form I, or II, or mixtures thereof is dissolved in an organic solvent or oil or mixtures thereof followed by further processing into said administration form which comprises a hydrophilic dispersant.

Another embodiment is a process for preparing an oily composition comprising astaxanthin which method comprises dissolving crystal Form I, or crystal Form II, or mixtures thereof directly in an edible oil and/or fish oil at temperatures between 100° C. and 230° C. for direct incorporation in fish feed pellets and other applications.

Carotenoids are a class of hydrocarbons (carotenes) and their oxygenated derivatives (xanthophylls) consisting of eight isoprenoid units. The carotenoid class of compounds is classified into two main groups: carotenes and xanthophylls. In contrast to carotenes, which are pure polyene hydrocarbons, such as beta.-carotene or lycopene, xanthophylls additionally contain functional moieties such as hydroxy, epoxy and oxo groups. Typical representatives of the group of xanthophylls are canthaxanthin, zeaxanthin and astaxanthin.

Astaxanthin is 3,3'-dihydroxy-β,β-carotene-4,4'-dione. Synthetic astaxanthin has the CAS number 7542-45-2 and is a 1:2:1 mixture of the diastereoisomers (3S, 3'S), (3R, 3'S) and 3R, 3'R). The astaxanthin isolated form natural sources has the CAS number of 472-61-7. Astaxanthin is a pigment found in many crustaceae, such as the common lobster (*Homarus gammarus*), in salmon (*Salamo salar*) in the feathers of flamingos (e.g. *Phoencopterus rubber*). Astaxanthin is used primarily as a feed ingredient for various animals, especially salmon, trout, shrimp, red sea bream, ornamental fish and poultry. Recently natural astaxanthin is also used as a food, nutriceutical or cosmetic additive with antioxidant properties.

Astaxanthin may be obtained by fermentation (Biotechnol. Letters 10(1988)609-614), or from microalgae disclosed in WO-A89/1997 and EP329754. WO-A86/6082 describes the isolation of astaxanthin from natural sources by extraction from crustacean shells. US2004253664 describes the production of carotenoids, xanthophylls and apo carotenoids utilizing eukaryotic microorganisms. An alternative source for extraction of natural astaxanthin is Aquasta™ which is a product made by fermenting a proprietary strain of the yeast *Phaffia rhodozyma*. A further method for obtaining astaxanthin is to utilize chemical synthesis such as in U.S. Pat. No. 5,654,488. Disclosures of each of these, and any other, documents mentioned herein are incorporated herein by reference in their entireties.

Screening for crystal forms of astaxanthin using small amounts (usually about 50 µl-1000 µl of an organic solvent solution of astaxanthin) is carried out in tubes or in well plate cups. The astaxanthin in the tubes/cups is crystallized by addition of an anti-solvent or by evaporation and the crystal structure is assessed by measurement of their characteristic Raman spectrum, X-ray powder diffraction pattern and other physical parameters. Controlled crystallization using small amounts of astaxanthin containing essentially various levels of different carotenoidal compounds, results unexpectedly, in two distinct crystal forms of astaxanthin which are formed individually or together in a mixture. Mixtures of crystal forms are assessed for content of the individual forms by comparing the measured Raman spectrum with the average individual spectra of the two forms at several known weight ratios for 'best fit'. The presence of the two individual forms in the mixture is reflected in the characteristic Raman spectrum, wherein no additional characteristic peaks are observed, other than the peaks of the spectra of the individual Form I and Form II, which contributes to the "best fit" spectrum. Factors relating to solvent removal and crystal recovery using polar, apolar, aprotic and protic solvents of industrial relevance in terms of toxicity (e.g. solvent residue), degree of solubility and stability of astaxanthin are examined. They show that the formation of astaxanthin crystal Form I or II is, surprisingly, independent of the solvent employed or the crystallization method but is essentially governed by the presence and concentration of carotenoidal compounds. Unexpectedly, the astaxanthin can exist in two distinct crystal forms and as a mixture of the two forms, depending on the conditions for preparing the crystals. This clearly indicates that two industrially useful crystalline forms and a mixture of the two forms may be prepared under controlled conditions from a solution of astaxanthin.

Known art for preparing astaxanthin compositions for fish feed and nutritional applications and other branches in the life science industry does not disclose the possibility of preparing specific crystal forms and in particular, mixtures of the two forms clearly characterised by X-ray powder diffraction pattern and Raman spectrum in addition to at least one other physical parameter such as melting point, solubility in organo-solvents, DSC scan. The crystal forms have different solubility in organo-solvents and oils which enable a wider choice for handling and formulating astaxanthin compositions. Furthermore, the crystal form can affect in vivo dissolution rate and allow higher (supersaturated) concentrations in oily administration vehicles which may provide higher uptake and bioavailability, after oral administration.

The X-ray diffractograms of the astaxanthin crystal forms are recorded using a Bruker D8 Advance model. D values are calculated form two-theta values at a wavelength of 1.5406 $10^{-10}$ m. Cu Kalpha 2 radiation is eliminated using software by Bruker, EVA Version 10.0. The Raman spectra are recorded with a Bruker FT-Spectrometer Bruker RFS 100/S with a Laser excitation wavelength of 1064 nm. DSC measurements are made with a Perkin Elmer Differential Calorimeter Model DSC 7.

Crystal Form I has a crystal habit with irregular shape and a red/red-brown appearance and a lower melting point, higher solubility and rate of dissolution in organo-solvents or oils compared to crystal Form II. Crystal Form I is characterized by its X-ray powder diffraction and Raman spectrum, as provided in FIGS. 1 and 2, respectively. Table 2 provides the characteristic X-ray powder diffraction of crystal Form I. The peak positions are given by the Angle 2-Theta° and corresponding d-value. The standard deviation in these positions may be ±5% or less. The intensity of the peaks are given by their Cps value and relative intensity related to the highest maximum. When the relative intensity is <5% the peak is designated as "vw" i.e. "very weak". Accordingly 5-15% as "w" (weak); 15-30 % as "m", (medium); 30-70% "s", (strong) and >70% "vs", (very strong).

TABLE 2

| Angle 2-Theta ° | D value $10^{-10}$ m | Qualtitative relative Intensity | Intensity Cps | Intensity % |
|---|---|---|---|---|
| 7.02 | 12.6 | vw | 5.7 | 3.9 |
| 11.02 | 8.0 | s | 49.7 | 34.2 |
| 11.71 | 7.6 | w | 20.6 | 14.2 |
| 12.36 | 7.2 | w | 8.41 | 5.8 |
| 13.70 | 6.5 | s | 74.5 | 51.2 |
| 14.09 | 6.3 | s | 72.8 | 50.1 |
| 14.44 | 6.1 | m | 35.3 | 24.3 |
| 14.86 | 5.96 | s | 75.9 | 52.2 |
| 15.88 | 5.58 | s | 84.5 | 58.2 |
| 16.31 | 5.43 | vs | 145 | 100 |
| 18.21 | 4.87 | vs | 127 | 87.5 |
| 18.70 | 4.74 | w | 21.7 | 14.9 |
| 20.53 | 4.32 | s | 90.1 | 62 |
| 20.94 | 4.24 | s | 44.8 | 30.8 |
| 21.09 | 4.21 | s | 44.9 | 30.9 |
| 21.84 | 4.07 | m | 32.2 | 22.1 |
| 22.05 | 4.03 | s | 43.6 | 30 |
| 23.54 | 3.78 | w | 12.3 | 8.5 |
| 24.82 | 3.58 | m | 24.5 | 16.9 |
| 25.40 | 3.50 | m | 28 | 19.2 |
| 26.22 | 3.40 | w | 10.9 | 7.5 |
| 27.67 | 3.22 | w | 8.75 | 6 |
| 28.79 | 3.10 | vw | 6.92 | 4.8 |
| 31.96 | 2.80 | vw | 6.61 | 4.6 |

Table 3 provides tle characteristic Raman spectrum of crystal Form I. The peak positions are given by the wave number in $cm^{-1}$. The standard deviation in these positions may be 5% or less. The intensity of the peaks are given by their Raman intensity value and relative intensity related to the highest maximum. When the relative intensity is <5% the peak is designated as "vw" i.e. "very weak"; accordingly 5-15% as "w" (weak); 15-30% as "m", (medium); 30-70% "s", (strong) and >70% "vs", (very strong).

TABLE 3

| Wave number $cm^{-1}$ | Qualitative relative Intensity | Raman emission intensity | Intensity (%) |
|---|---|---|---|
| 372.8 | s | 0.179 | 35.8 |
| 347.7 | m | 0.122 | 24.4 |
| 333.3 | m | 0.138 | 27.6 |
| 312.1 | s | 0.184 | 36.8 |
| 289.9 | s | 0.231 | 46.3 |
| 234.9 | m | 0.130 | 26.1 |
| 194.4 | s | 0.311 | 62.3 |
| 178.1 | s | 0.326 | 65.3 |
| 132.8 | vs | 0.499 | 100 |
| 81.6 | m | 0.101 | 20.2 |

Crystal Form I is stable in the dry form. This crystal may exhibit properties desirable over those of Form II, such as enhanced solubility in organo-solvents and oils.

Crystal Form II has a crystal blade/sheet-like habit and blue/violet appearance and a higher melting point and lower solubility in oil and organic solvents compared to crystal Form I. Crystal Form II is characterized by their X-ray powder diffraction and Raman spectrum as outlined in FIGS. 3 and 4, respectively. In Table 4 a typical X-ray powder diffraction of crystal Form II is provided. The peak positions are given by the Angle 2-Theta° and corresponding d-value. The standard deviation in these positions may be ±5% or less. The intensity of the peaks is given by their Cps value and relative intensity related to the highest maximum. When the relative intensity is <5% the peak is designated as "vw" (very weak); accordingly 5-15% as "w" (weak); 5-30% as "m", (medium); 30-70% "s" (strong) and >70% "vs", i.e. (very strong).

TABLE 4

| Angle 2-Theta ° | d value $10^{-10}$ m | Qualtitative relative Intensity | Intensity Cps | Intensity % |
|---|---|---|---|---|
| 8.37 | 10.6 | w | 12.1 | 5 |
| 9.82 | 9.0 | vw | 9.0 | 3.7 |
| 10.26 | 8.6 | w | 18.6 | 7.7 |
| 12.32 | 7.2 | m | 66.1 | 27.3 |
| 13.49 | 6.6 | s | 118.0 | 48.8 |
| 13.69 | 6.5 | s | 129.0 | 53.1 |
| 16.15 | 5.48 | s | 77.8 | 32.1 |
| 16.58 | 5.34 | s | 99.2 | 40.9 |
| 16.81 | 5.27 | m | 41.9 | 17.3 |
| 18.82 | 4.71 | w | 36.0 | 14.8 |
| 19.76 | 4.49 | m | 38.0 | 15.7 |
| 20.27 | 4.38 | vs | 242.0 | 100 |
| 20.62 | 4.30 | w | 23.1 | 9.5 |
| 21.53 | 4.12 | s | 82.7 | 34.1 |
| 22.10 | 4.02 | w | 22.0 | 9.1 |
| 22.86 | 3.89 | m | 51.9 | 21.4 |
| 23.54 | 3.78 | w | 21.3 | 8.8 |
| 23.83 | 3.73 | w | 17.1 | 7.1 |
| 24.63 | 3.61 | m | 55.3 | 22.8 |
| 25.00 | 3.56 | s | 148.0 | 61.3 |
| 25.53 | 3.49 | w | 31.8 | 13.1 |
| 25.87 | 3.44 | w | 21.5 | 8.9 |
| 26.64 | 3.34 | m | 41.4 | 17.1 |
| 26.80 | 3.32 | m | 48.7 | 20.1 |
| 27.65 | 3.22 | s | 75.8 | 31.3 |
| 29.24 | 3.05 | w | 12.8 | 5.3 |
| 29.92 | 2.98 | w | 14.8 | 6.1 |
| 31.79 | 2.81 | w | 20.3 | 8.4 |
| 32.38 | 2.76 | w | 27.9 | 11.5 |
| 32.58 | 2.75 | w | 25.3 | 10.4 |
| 34.88 | 2.57 | w | 30.9 | 12.8 |

In Table 5 a typical Raman spectrum for crystal Form II is provided. The peak positions are given by the wave number in $cm^{-1}$. The standard deviation in these positions may be ±5% or less. The intensity of the peaks is given by their Raman intensity value and relative intensity related to the highest maximum. When the relative intensity is <5% the peak is designated as "vw" (very weak); accordingly 5-15% as "w" (weak); 15-30% as "m", (medium); 30-70% "s", (strong) and >70% "vs", (very strong).

TABLE 5

| Wave number $cm^{-1}$ | Qualitative relative Intensity | Raman emission intensity | Intensity (%) |
|---|---|---|---|
| 376.7 | s | 0.267 | 65.9 |
| 338.1 | m | 0.110 | 27.1 |
| 314.0 | s | 0.151 | 37.2 |
| 306.0 | s | 0.214 | 52.8 |
| 290.9 | s | 0.230 | 56.8 |
| 207.0 | vs | 0.405 | 100 |
| 180.0 | s | 0.249 | 61.5 |
| 138.6 | s | 0.361 | 89.1 |
| 107.7 | s | 0.279 | 68.9 |
| 93.3 | s | 0.238 | 58.7 |

Figure 5:
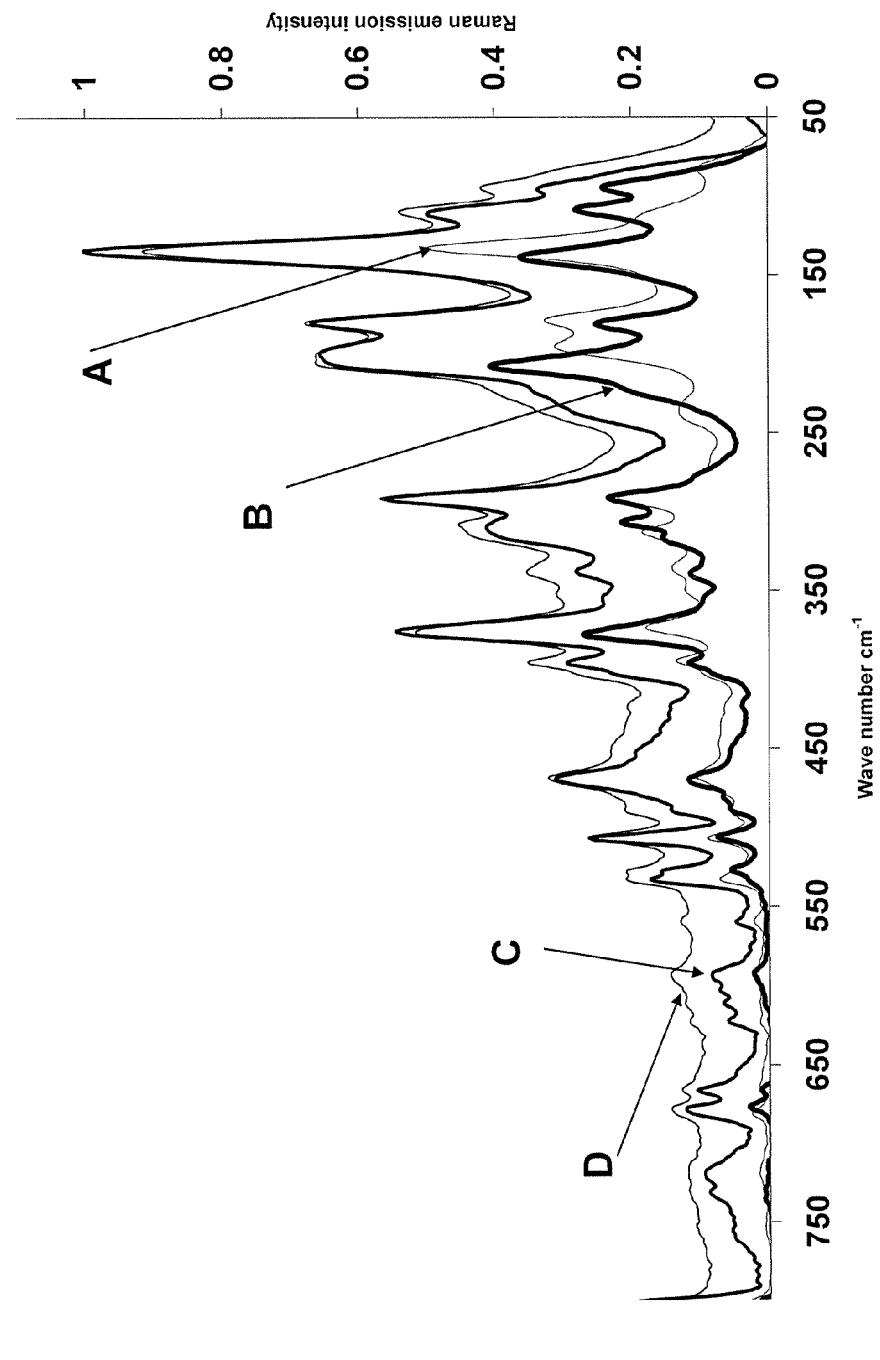
FIG. 5 shows an exemplary Raman spectrum of a mixture comprising crystal Form I and crystal Form II of astaxanthin in comparison with a calculated spectrum as derived from the individual spectra of crystal Form I and Form II of astaxanthin.

FIG. 5 portrays a Raman spectrum of a mixture comprising crystal Form I and Form II in a weight ratio of 0.55:0.45.

To prepare the desired crystal form or mixtures of the two forms, astaxanthin which comprises at least 93% by weight of all-trans-astaxanthin may be dissolved in a suitable solvent and used as the starting material. Appropriate amounts of at least one carotenoidal compound may be added. Alternatively the carotenoidal compound/s may be formed in situ by controlling the conditions e.g. temperature and oxidation of the solution preceding and/or during crystallization. For instance, the carotenoidal compounds can be formed in-situ during or after dissolution of astaxanthin in high boiling point solvents such as toluene, edible oils and alkanols. Seeds comprising the desired crystal form may be added to the crystallization medium to accelerate the crystallization and to increase the yield of the desired crystal form.

Alternatively, the desired crystal form or mixture of Form I and Form II may be prepared by controlling the method for the manufacture, extraction or purification steps for astaxanthin wherein the final crystallization solution comprises a sufficient amount of at least one carotenoidal compound/s essentially within the range desired for forming crystal Form I, Form II or physical mixtures of Form I and Form II as described in this specification. Crystal Form I or mixtures of Form I and Form II may also be prepared from a solution with highly pure astaxanthin, (i.e. greater than 95%) followed by treatment of the solution with e.g. heat and/or light to cause the formation of a sufficient amount of carotenoidal compound to obtain essentially crystal Form I, or mixtures of Form I and Form II after final crystallization.

It should be understood that the aforementioned crystallization methods may be carried out, for example, after synthesis for preparation of either Form I or Form II crystals. Alternatively, they may also be carried out in the purification or extraction steps for astaxanthin crystals (as part of chemical synthesis or isolation of the astaxanthin compound from natural products) wherein at least one crystallization step for preparing astaxanthin crystal, or a (re)crystallization procedure utilizing solvents is employed.

The starting solutions for preparing the astaxanthin crystal form or mixture of the crystal forms do not need to contain the exact amount of carotenoidal compounds (within the range desired in a particular crystal form), as long as there is a sufficient concentration at the start of crystallization, concomitant with crystals of Form I or II or mixtures thereof as disclosed. Dissolving the astaxanthin in boiling solvents may result in sufficient formation of carotenoidal compounds as by-products. Furthermore by selecting the most appropriate solvent, temperature and conditions for washing, the unassociated carotenoidal compounds may be removed. Addition of seeds comprising crystal Form I or crystal Form II to a crystallization solution may further accelerate the formation of the desired form with higher yields.

Suitable carotenoidal compounds that may be added to all-trans-astaxanthin, individually or for example as a mixture for preparing the desired astaxanthin crystal Form I, or II, or a mixture thereof are synthetic astaxanthin derivatives e.g. etherified or esterified, oxidation or hydrogenation products, cis-isomers of astaxanthin. The term includes by-products obtained during synthesis and crystallization of astaxanthin or during the extraction process of astaxanthin from natural sources. The formation of the carotenoidal compounds may be the result of performing the synthesis under sub-optimal conditions or may be the result of performing the synthesis, extraction or crystallization procedures under conditions which allow control of the carotenoidal compound concentration at the desired level. One or a mixture of a preferred carotenoidal compound may be selected from members of the group of carotenoidal compounds comprising (e.g., consisting of) 9-cis, 13-cis -astaxanthin and other cis-astaxanthin derivatives (e.g. 15-cis-astaxanthin), astacene (i.e. $\beta,\beta$ carotene-3,3',4,4'-tetrone with CAS nr 514-76-1), semi-astacene (3-hydroxy-$\beta,\beta$-carotene-3',4,4'-trione) and the C-25 aldehyde (all-trans-3-hydroxy-4-oxo-12'-apo-beta-caroten-12'-al, with CAS Nr. 72523-68-3). They can be used alone or in any combination.

There are several crystallization methods based on similar principles that may be considered to prepare crystal Form I, Form II or mixtures comprising Form I and Form II, starting from solutions differing in carotenoidal compound profile and concentration. Suitable crystallization methods that may be considered by a skilled person include but are not limited to the following methods. In general, suitable solvents to prepare the solutions are solvents which dissolve at least 1 mg/ml, preferably up to 10-50 mg/ml of astaxanthin at the temperature when crystallization is initiated. When anti solvents are used, suitable anti solvents are solvents which dissolve less than 1 mg/ml at the temperature for crystallization and which are miscible with the solvent in which the astaxanthin is dissolved.

Starting from an apolar aprotic organic solution of astaxanthin under controlled temperature conditions, crystallization is induced by removal of the solvent from the solution, optionally by simultaneous exchange with a miscible polar anti-solvent. A preferred apolar aprotic solvent is dichloromethane. Alternative chlorinated apolar aprotic solvents are e.g. chloroform, trichloroethane. Suitable non -chlorinated alternatives are dimethoxymethane, diethoxyethane and dioxacyclopentane. An exemplary preferred polar anti-solvent is methanol or other alkanols such as ethanol, n-propanol, isopropanol, n-butanol and tert-butanol.

Crystals comprising Form I or II may also be obtained by removal of the solvent from an astaxanthin solution in a polar aprotic or polar protic solvent by evaporation. Solvents which have a high solubility for astaxanthin and a low boiling point are preferred. Examples are THF and pyridine.

Another method to induce crystallization is cooling of an (over) saturated solution in an apolar aprotic solvent. Exemplary preferred apolar aprotic solvents are dichloromethane, toluene or alternative chlorinated apolar aprotic solvents. Polar solvents such as tetrahydrofuran (THF), N-methylpyrrolidone (NMP), N-ethylpyrrolidone (NEP) and pyridine which have a high solubility for astaxanthin may be considered as well. The crystallization rate and yield of the desired crystal Form may be increased by adding seeds of the pure form to the crystallizing solution.

Crystals comprising Form I or II can also be obtained by dilution of a solution of astaxanthin containing the desired concentrations of all-trans-astaxanthin and carotenoidal compounds in a apolar aprotic, polar aprotic or polar protic solvent by adding a miscible polar anti solvent. Examples of apolar aprotic solvents are dichloromethane, toluene or alternative chlorinated solvents. Anti solvents are in that case alkanols like methanol. Examples of suitable polar solvents are THF, NMP and pyridine. As anti solvent, alkanols or preferably water can be used.

The resulting crystals are harvested by e.g. filtration, spontaneous sedimentation or centrifugation methods known in the art, optionally washed with a suitable (anti)solvent, preferably with a cold alkanol (preferably methanol, for example) and dried, preferably under vacuum. The resulting crystals may be milled to obtain the desired particle size for further processing.

Using the methods described above the chlorinated solvents may be replaced by dimethoxymethane, diethoxyethane or dioxacyclopentane.

As the carotenoidal compound concentration in the crystallizing solution increases from 0% up to about 7 mol % and the remaining carotenoids is all-trans -astaxantin, crystal Form II is predominantly formed, and the presence of the other crystal Form I may be below detectable levels of less than 5%. At about the 7 mol % carotenoidal compound level and the remaining carotenoids is all-trans-astaxanthin, minor amounts of crystal Form I may be formed in the presence of major amounts of crystal Form II. When the mol % of carotenoidal compound/s present in the solution increases from about 7 mol % to about 17 mol % and the remaining fraction of total carotenoids is all-trans-astaxanthin, mixtures comprising crystal Form I and II are obtained, wherein the ratio of Form I to II follows the increase in carotenoidal compounds. At about the 17 mol % carotenoidal compound level and the remaining fraction of total carotenoids is all-trans-astaxanthin, minor amounts of crystal Form II may be formed in the presence of major amounts of crystal Form I. Above about 17 mol % of tle carotenoidal compound/s and the remaining fraction of total carotenoids is all-trans-astaxanthin, crystal Form I predominates and the presence of crystal Form II may be below detectable levels of less than 5%. The extent of formation of crystal Form I and/or Form II depends, however, on the overall crystallization conditions.

Dependent on the carotenoidal level in the crystallizing solution and crystallization conditions mixtures of crystal Form I and I may contain from 0% to 100% of Form I and 100% to 0% of Form II, or from 0.1% to 99.9% of Form I and 99.9% to 0.1% of Form II, or from 5% to 95% of Form I and 95% to 5% of Form II, or from 10% to 90% of Form I and 90% to 10% of Form II, or from 20% to 80% of Form I and 80% to 20% of Form II.

In preferred examples when the carotenoidal compounds are predominantly cis-astaxanthin, crystals of Form I may be formed containing at least about 17 mol % cis-astaxanthin (preferably, 9-cis or 13-cis or mixtures thereof). Thus it is possible to prepare astaxantn crystal Form I comprising up to nearly 100% astaxanthin which have beneficial solubility characteristics in organo-solvents and oils and a lower melting point.

The content of carotenoidal compounds may be higher or lower in the starting solution compared to the resulting crystals, depending on the crystallization procedure applied. When increased temperatures are used, the concentration of carotenoidal compound in the solution and the crystals would increase whilst the all-trans -astaxanthin content of the crystals would decrease. When milder temperature conditions and/or different crystallization methiods are used, the carotenoidal compound level may be lower in the crystals. In parallel, the all-trans-astaxanthin content of the crystals would increase. Furthermore, the washing step employed in the final stage for preparing the desired astaxanthin crystal Form may remove unassociated carotenoidal compounds from the astaxanthin crystals.

Crystal Form I, prepared from solutions comprising all-trans-astaxanthin and above about 17 mol % of carotenoidal compound/s, may comprise all-trans-astaxanthin along with at least about 13 mol % of preferably, at least one member of the group of carotenoidal compounds consisting of cis-astaxanthin, semi astacene, astacene or C-25 aldehyde. More preferred are the 9-cis or 13-cis-astaxanthin or 15-cis-astaxanthin on their own or in a mixture. When all the crystals are Form I and the astaxanthin comprises all-trans-astaxanthin and only 9-cis or 13-cis-astaxanthin, according to the purity definition adopted in aquaculture (Determination of stabilized astaxanthin in premixes and fish feeds—version 1.1, Roche Vitamins Ltd and references therein, J. Schierle, N. Faccin, V. Riegert), the astaxanthin may be regarded as 100% pure.

Crystal Form II prepared from a solution comprising all-trans-astaxanthin and a carotenoidal compound concentration from 0% up to a maximum of) about 7 mol % may comprise all-trans-astaxant with less than about 7 mol % of preferably, at least one member of the group of carotenoidal compounds comprising (e.g., consisting of) 9-cis-astaxanthin, 13-cis-astaxanthin, 15-cis-astaxanthin, semi astacene, astacene or C-25 aldehyde. More preferred are the 9-cis or 13-cis-astaxanthin on their own or in a mixture. Astaxanthin meeting the specifications described in the US-FDA data base 21 CFR 73.35, comprising not more than 4% of "Total carotenoids other than astaxanthin", and in the form of crystal Form II is covered in his disclosure. For the avoidance of doubt, the "total carotenoids other than astaxanthin" are defined in instant disclosure as "carotenoidal compound". Preferred, is astaxanthin meeting the FDA specification, in which the "Total carotenoids other than astaxanthin" comprise (e.g., consist of) carotenoidal compounds selected from the group comprising (e.g., consisting of) at least one cis-astaxanthin, astacene, semi-astacene and C-25 aldehyde. More preferred is an astaxanthin meeting the FDA specification in which said "Total carotenoids other than astaxanthin" comprise (e.g., consist of) carotenoidal compounds selected from the group consisting of 9-cis-astaxanthin, 13-cis-astaxanthin and 15-cis-astaxanthin.

Crystal Forms may contain other compounds such as solvent residues, heavy metal and degradation products which are present in minor, permitted amounts.

Crystal Form I, Form II and mixtures of the two forms are suitable for incorporation as such in solid, semi solid formulations suitable for administration to an organism. Examples of solid forms are tablets, granulates, pellets, capsules, powders, etc. Examples of semi-solid forms are creams, ointments, gels, suspensions and lotions. They particularly include particulate micronised suspensions of crystal Form I or Form II or mixtures of Form I and II in an oily vehicle. Preferably the crystals are in the average size range between 1-5 µm.

Preferred administration forms which may be prepared using crystal Form I are the oil-dispersible compositions comprising astaxanthin and methods of preparation thereof, described in WO03/102116. Crystal Form I or Form II or mixtures thereof designated by X-ray and Raman spectroscopy as described herein may also be used for preparing the water-dispersible compositions comprising astaxanthin that are described in U.S. Pat. No. 2,861,891, U.S. Pat. No. 5,364,563 and U.S. Pat. No. 6,296,877, the disclosures of which are hereby incorporated by reference in their entireties.

The usual method to prepare solid compositions and formulations comprising astaxanthin is to dissolve the crystal Form I, Form II or mixtures thereof in an organic, water miscible or water immiscible solvent or mixtures thereof in the presence of suitable excipients, followed by removal of the solvent by either dilution in water or evaporation techniques described in WO03/102116. Crystal Form I or II may be directly employed as such and dissolved in oily solutions of astaxanthin by applying energy.

The solvents used to prepare solutions and for processing of the astaxanthin crystal Form I or II or mixtures thereof into dry astaxanthin compositions may be water miscible or water immiscible. Examples of water miscible and immiscible solvents include the examples of solvents used for crystallization of the crystalforms that are listed above. By the application of heat/pressure, an anti-solvent employed during crystallization under normal pressures and ambient temperatures may be used as solvent for astaxanthin (e.g isopropanol/water)

Preferred examples of excipients are dispersants, polymers and synthetic natural gums and cellulose derivatives which may be either hydrophilic or lipophilic.

The solid astaxanthin composition comprises between 2.5 wt % to 25 wt %, preferably 5 wt % to 15 wt %, more preferably 7.5 wt % to 12.5 wt % of total astaxanthin. The amount of dispersant used in the composition is preferably between 50 wt % to 97.5 wt %. Varying amounts of excipients may be used as bulking agents to make up the required weight.

Suitable lipophilic dispersing agents are those described in WO 03/102116 as lipophilic polymers suitable for preparing oil soluble carotenoid compositions and used as nutrient or as pharmaceutical additives as lipoplifiic coating material to modify the drug release of oral solid dosage forms. Suitable dispersing agents may be selected from particular members of the group comprising (e.g., consisting of) ethylcelluloses, synthetic and natural resins, rosins and gums.

Suitable hydrophilic dispersants are those described in U.S. Pat. No. 2,861,891, U.S. Pat. No. 5,364,563 and U.S. Pat. No. 6,296,877 as water soluble dispersants and processes which are suitable for preparing water-dispersible carotenoid compositions. The hydrophilic dispersants include but are not limited to protective colloids of low- and high-molecular-weight components of, for example, gelatin, fish gelatin, starch, dextrin, plant proteins, pectin, gum arabic, casein, caseinate or mixtures of these, the protein -containing protective colloids, in particular non-gelling low-molecular-weight protein hydrolysates and higher-molecular-weight gelling gelatins being preferred. These and other poly(vinylalcohol), polyvinylpyrrolidone, methyl cellulose, carboxymethyl cellulose, hydroxypropyl cellulose and alginates can also be used. The mean molecular weight of the low-molecular-weight protective colloid component is, for example, preferably from 10,000 to 50,000, in particular from 15,000 to 30,000, whereas the high-molecular-weight component has a mean molecular weight of preferably greater than 60,000. The proportion of the low-molecular-weight protective colloid component is from, for example, 5 to 95% by weight, preferably from 20 to 80% by weight, in particular from 30 to 60% by weight. To increase the mechanical stability of the end product, it is expedient to admix the colloid with a softener, such as sugars or sugar alcohols, For example, sucrose, glucose, lactose, invert sugar, sorbitol, mannitol or glycerol as described in U.S. Pat. No. 6,296,877. Further hydrophilic dispersants may be selected from members of the group comprising (e.g., consisting of) PEG polyethylengylcol) with MW 4000-6000, polyvinylpyrrolidone, polyvinylalcohol, crospovidone, polyvinylpyrrolidone-polyvinylacetate copolymer, hydroxypropylmethylcellulose (HMPC), hydroxypropylcellulose (HPC), hydroxypropylmethylcellulose phthalate (HPMCP), polyacrylates and polymethacrylates.

The solvent or solvent mixture is removed by e.g. spray drying, freeze drying, freeze spray drying, spray granulation or supercritical fluid expansion.

The crystal forms are suitable for preparing compositions comprising J or H aggregates of astaxanthin as described in U.S. Pat. No. 6,827,941, the disclosure of which is hereby incorporated by reference in its entirety, which are precipitated by adding the organic solvent solution prepared from astaxanthin crystal Form I, Form II or mixtures thereof to excess water.

Crystal Form I may be used to, for example, manufacture the water dispersible compositions according to U.S. Pat. No. 6,093,348, the disclosure of which is hereby incorporated by reference in its entirety, wherein the carotenoid is dispersed with suitable surfactant/hydrocolloids and melted at high temperatures and pressures to form an emulsion.

EXAMPLES

The following representative examples (1-7) illustrate methods to prepare astaxanthin crystal Form 1 or Form II or defined mixtures thereof starting from organic liquid solutions with different polarity comprising known amounts of all-trans -astaxanthin and at least one specified carotinoidal compound. Examples (7-9) illustrate the method wherein crystal Form I and/or crystal Form II or defined mixtures thereof may be incorporated as such in administration forms. Examples (10-13) illustrate the method wherein crystal Form I or crystal Form II or defined mixtures thereof may be dissolved in solvents for preparing administration and nutritional compositions.

For preparing the desired crystal form, astaxanthin was purchased from Sigma (natural astaxanthin) and Dr. Ehrenstorfer (synthetic astaxanthin, analytical grade). The purity of the compound was determined by HPLC measurements and characterised by X-ray diffraction and Raman spectroscopy. Ultra pure astaxanthin may also be obtained from less pure astaxanthin by means of preparative HPLC.

Example 1

40 mg of astaxanthin (97.2 mol % all-trans-astaxanthin and 1.6 mol % 9-cis-astaxanthin and 1.2 mol % 13-cis-astaxanthin) is dissolved in 2 ml dichloromethane (DCM) at 30° C. and processed into crystals by solvent removal under vacuum, Raman spectrum shows the presence of crystal Form II as in FIG. 4. The X-Ray diffraction pattern is shown in FIG. 3. HPLC analysis of the crystals show 99.2 mol % all-trans-astaxanthin, 0.4 mol % 9-cis-astaxanthin, 0.4 mol % 13-cis -astaxanthin, corresponding with a carotenoidal compound level of about 0.8 mol %.

Example 2

20 mg analytical grade astaxanthin (97.2 mol % all-trans-astaxanthin and 1.6 mol % 9-cis-astaxanthin and 1.2 mol % 13-cis-astaxanthi) is dissolved in 1 ml pyridine and heated at 70° C. for 30 min. After addition of 8.0 ml cold water, the formed crystals are washed with water and the Raman spectrum shows the presence of crystal Form I as seen in the spectrum in FIG. 2. The X-Ray diffraction pattern is shown in FIG. 1. HPLC determination confirms the total amount of all-trans-astaxanthin and cis-astaxanthin isomers to be 100%. The astaxanthin comprises 78 mol % all-trans-astaxanthin, 3 mol % 9-cis-astaxantlhn and 19 mol % 13-cis-astaxanthin. The level of carotenoidal products is about 22 mol %. Similarly, when the pyridine solution is heated at 80° for 40 min, 28 mol % 13-cis -astaxanthin is formed and the resulting crystal is assigned as astaxanthin crystal Form I by the characteristic X-ray diffraction pattern and Raman spectrum.

Example 3

20 mg of astaxanthin comprising 97.2 mol % all-trans-astaxanthin and 2.8 mol % cis-astaxant (further comprising 1.6 mol % 9-cis-astaxanthin and 1.2 mol % 13-cis-astaxant) is dissolved in 1.0 ml pyridine at room temperature (solution 1).

20 mg of astaxanthin from Example 2 comprising 72 mol % all-trans-astaxanthin and 28 mol % 13-cis-astaxantliin are dissolved in 1.0 ml pyridine at room temperature (solution 2). The two solutions are mixed at several ratios and 0.6 ml cold water is added, the formed crystals are collected by filtration, washed with 2 ml water and a Raman spectrum is recorded after drying. The results are summarized in Table 6.

TABLE 6

| Preparation crystallization solution | | Carotenoidal compound level in crystallization solution | Crystal Form | |
|---|---|---|---|---|
| Volume Solution 1 | Volume Solution 2 | | | |
| (μl) | (μl) | (mol %) | I | II |
| 200 | 0 | 3.00 | 0.0 | 1.0 |
| 200 | 5 | 3.61 | 0.0 | 1.0 |
| 200 | 10 | 4.19 | 0.0 | 1.0 |
| 200 | 20 | 5.27 | 0.43 | 0.57 |
| 200 | 50 | 8.00 | 0.55 | 0.45 |
| 200 | 100 | 11.33 | 0.7 | 0.3 |
| 200 | 200 | 15.50 | 1.0 | 0.0 |
| 60 | 200 | 22.23 | 1.0 | 0.0 |
| 20 | 200 | 25.77 | 1.0 | 0.0 |
| 0 | 200 | 28.00 | 1.0 | 0.0 |

Example 3 clearly shows that by using a, polar protic solvent e.g. pyridine, the formation of either crystal Form I or II or mixtures thereof depends mainly on the level of carotenoidal compounds in the solution. FIG. 5 portrays a Raman spectrum of a mixture comprising crystal Form I and Form II in a weight ratio of 055:0.45.

Alternatively the concentration of carotenoidal compounds may be controlled by e.g. adding known amounts of a carotenoidal compound sufficient to associate with the crystal lattice of all-trans-astaxanthin and/or formed in-situ by heating the pyridine solution causing formation of said carotenoidal compound as shown in Ex 2, before adding the anti-solvent water. Alternatively, the desired crystal Form or mixture may be prepared by evaporation of the solution, cooling the solution with or without using seeds of either crystal Form I or II Example 4

35.66 mg astaxanthin comprising 97.2 mol % all-trans-astaxanthin, 1.6 mol % 9-cis-astaxanthin and 1.2 mol % 13-cis-astaxanthin and 3.61 mg of a carotenoidal compound comprising astacene are dissolved in 24 ml DCM and the DCM is removed by distillation and simultaneously replaced by methanol. The formed crystals are harvested and washed with cold methanol and dried under vacuum. Raman spectrum shows the presence of crystals comprising crystal Form I as well as crystal Form II in a ratio of 6:4. (Raman spectra of both pure crystal Forms are averaged in several weight ratios and accorded with the measured spectrum). HPLC analysis of the crystals show 85.4% w/w all-trans-astaxanthin, 0.4% w/w 9-cis -astaxanthin, 1.0% w/w 13-cis-astaxanthin, 7.6% w/w astacene, 1.9% w/w semi-astacene and 3.6% w/w C-25 aldehyde corresponding with a carotenoidal compound level of about 17 mol %.

Example 5

40.3 mg astaxanin comprising 80% w/w all-trans-astaxanthin, 2.7% w/w 9-cis-astaxanthin, 2.7% w/w 13-cis-astaxanthin, 0.8% w/w astacene, 5.5% w/w semi astacene and 8.7% w/w C-25 aldehyde are dissolved in 24 ml DCM and heated to boiling. 40 ml MeOH is added dropwise as the DCM is removed by distillation. The resulting crystals are filtered and then washed witlh MeOH at 0° C. and the crystals are dried in vacuum overnight at RT. Raman spectrum shows the presence of Form I crystals. HPLC analysis of the crystals show 87% w/w all-trans-astaxanthin, 1.3% w/w 9-cis-astaxanthin, 1.5% w/w 13-cis-astaxanthin, 0.9% w/w astacene, 6.2% w/w semi-astacene and 2.8% C-25 aldehyde, corresponding to carotenoidal compound level of about 16 mol %.

Example 6

196.7 mg astaxanthn comprising 80% w/w all-trans-astaxanthm, 2.7% w/w 9-cis-astaxanthin, 2.7% w/w 13-cis-astaxantin, 0.8% w/w w/w astacene, 5.5% w/w semi astacene and 8.7% w/w C-25 aldehyde and 203.3 mg astaxanthin 97.2% w/w all-trans-astaxanthin, 1.6% w/w 9-cis-astaxanthin and 1.2% w/w 13-cis-astaxanthin are dissolved in 24 ml DCM. The DCM is removed by distilation and simultaneously replaced by 40 ml MeOH as in Example 1. Raman spectrum shows the presence of crystals comprising crystal Form I as well as Form II in the ratio of 7:3. HPLC analysis of tlhe crystals show 91% w/w all-trans-astaxanthin and carotenoidal compounds comprising 0.9% w/w 9-cis-astaxanhin, 0.5% w/w 13-cis-astaxanthin, 0.4% w/w astacene, 3.5% w/w semi-astacene and 3.5% C-25 aldehyde corresponding with a carotenoidal compound level of about 12 mol %.

Example 7

Analogue the preceding examples alternative starting solvents, instead of pyridine, like chloroform, trichloroethane, dimethoxyrnethane, diethoxyethane and dioxacyclopentane THF, NMP, NEP and toluene can be used. The crystals of crystal Form I or crystal Form II can be obtained, dependent on the concentration of carotenoidal compound in the crystallization solution (at the start of crystallization) comprising all-trans-astaxanthin, from the optionally heated solution by either i) removing the solvent by evaporation, optionally with simultaneous replacement with an miscible anti solvent ii) addition of a miscible anti solvent to the solution or iii) cooling of an (over-saturated) solution. As the carotenoidal compound concentration in the crystallizing solution increases from 0% up to about 7 mol % and the remaining fraction of total carotenoids is all-trans-astaxanthin, crystal Form II is predominantly formed, the presence of the other crystal Form I may be below detectable levels of less than 5%. At about the 7 mol % carotenoidal compound level and the remaining fraction of total carotenoids is all-trans-astaxanthin, minor amounts of crystal Form I may be formed in the presence of major amounts of crystal Form II. When the mol % of carotenoidal compound/s present increases from about 7 mol % to about 17 mol % and the remaining fraction of total carotenoids is all-trans -astaxanthin, mixtures comprising crystal Form I and II are obtained wherein the ratio of Form I to II increases. At about the 17 mol % carotenoidal compound level and the remaining fraction of total carotenoids is all-trans-astaxanthin, minor amounts of crystal Form II may be formed in the presence of major amounts of crystal Form I. Above about 17 mol % of the carotenoidal compound/s and the remaining fraction of total carotenoids is all-trans-astaxanthin, crystal Form I predominates and the presence of the other crystal Form II may be below detectable levels of less than 5%. The extent of formation of crystal Form I and/or Form II depends, however, on the overall crystallization conditions.

Example 8

10 g of astaxanthin crystal Form I or Form II are mixed with 90 g soy bean oil. The crystals are milled and the resulting micronised suspension is suitable for preparation of powder formulations or can be directly dissolved in oil using a flash heating procedure followed by cooling with an excess of an oil phase or water phase comprising an emulsifier.

Example 9

10 g of astaxanthin crystal Form I or Form II are mixed with 20 g starch. The powder is further processed into a flowable granulate suitable for capsule filing and tabletting.

Example 10

In a heatable receiving flask, 4 g of astaxanthin crystal Form I or Form II and 1.54 g of peanut oil are suspended in a solution of 1.23 g of ethoxyquin in 28.8 g of isopropanol/ water (88/12, w/w) at 30° C. This suspension is mixed at a mixing temperature of 170° C. with 58.7 g of isopropanol/ water (88/12, w/w) with a residence time of 0.2 seconds. The resulting molecularly dispersed astaxanthin solution immediately afterward enters a further mixing chamber. 11.34 g of an aqueous gelatin solution, adjusted to pH 9 which, in addition to 8.4 g of gelatin A (100 Bloom, M.W.=94,000), containing 4.2 g of Gelita Sol P (M.W.=21,000) and 9.2 g of sucrose, is added to precipitate the astaxanthin, at 45° C., in colloidally dispersed form.

Example 11

A powder composition is prepared by dissolving 1 g the astaxanthin crystal Form I, with 8 g ethylcellulose N4 (The Dow Chemical Company) and 1 g alpha -tocopherol in 90 g dichloromethane (Fluka), followed by removal of the solvent to produce a granulate, using spray granulation.

Example 12

A powder composition is prepared by dissolving 0.80 g the astaxanthin crystal Form II with 8.4 g ethylcellulose N4 (The Dow Chemical Company) and 0.80 g alpha-tocopherol in 90 g dichloromethane (Fluka), followed by removal of the solvent to produce a granulate, using spray granulation.

Example 13

620 mg astaxanthin (crystal Form II) is mixed with 200 ml THF at room temperature and filtered. 50 ml of the THF solution is added dropwise to 250 ml water during 30 min. Mainly colloidal precipitates of astaxanthin aggregates are formed which can be harvested by filtration.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A mixture consisting essentially of crystal forms of astaxanthin comprising:
    a) Crystal Form I having an X-ray diffraction pattern comprising the following interlattice plane interval d in $10^{-10}$ m: 8.0±0.1, 6.5±0.05, 6.3±0.05, 6.1±0.05, 5.96±0.05, 5.58±0.05, 5.43±0.05, 4.87±0.05, 4.32±0.05, 4.24±0.05, 4.21±0.05, 4.07±0.05, 4.03±0.05, 3.58±0.05, 3.50±0.05, and
    b) Crystal Form II having an X-ray diffraction pattern comprising the following interlattice plane interval d in $10^{-10}$ m: 7.2±0.1, 6.6±0.05, 6.5±0.05, 5.48±0.05, 5.34±0.05, 5.27±0.05, 4.49±0.05, 4.38±0.05, 4.12±0.05, 3.89±0.05, 3.61±0.05, 3.56±0.05, 3.34±0.05, 3.32±0.05, 3.22±0.05.

2. A mixture according to claim 1 consisting essentially of:
    99.9% to 0.1% by weight of the crystalline form of astaxanthin designated crystal Form I and
    0.1% to 99.9% by weight of the crystalline form of astaxanthin designated crystal Form II.

3. A mixture according to claim 1 consisting essentially of:
    95% to 5% by weight of the crystalline form of astaxanthin designated crystal Form I and
    5% to 95% by weight of the crystalline form of astaxanthin designated crystal Form II.

4. A mixture according to claim 1 consisting essentially of:
    10% to 90% by weight of the crystalline form of astaxanthin designated crystal Form I and
    90% to 10% by weight of the crystalline form of astaxanthin designated crystal Form II.

5. A mixture according to claim 1 consisting essentially of:
    20% to 80% by weight of the crystalline form of astaxanthin designated crystal Form I and
    80% to 20% by weight of the crystalline form of astaxanthin designated crystal Form II.

6. A composition comprising a crystalline form of astaxanthin designated crystal Form I having
    an X-ray diffraction pattern comprising the following interlattice plane interval d in $10^{-10}$ m: 8.0±0.1, 6.5±0.05, 6.3±005, 6.1±0.05, 5.96±0.05, 5.58±0.05, 5.43±0.05, 4.87±0.05, 4.32±0.05, 4.24±0.05, 4.21±0.05, 4.07±0.05, 4.03±0.05, 3.58±0.05, 3.50±0.05.

7. A composition comprising a crystalline form of astaxanthin designated crystal Form II having
    an X-ray diffraction pattern comprising the following interlattice plane interval d in $10^{-10}$ m: 7.2±0.1, 6.6±0.05, 6.5±0.05, 5.48±0.05, 5.34±0.05, 5.27±0.05, 4.49±0.05, 4.38±0.05, 4.12±0.05, 3.89±0.05, 3.61±0.05, 3.56±0.05, 3.34±0.05, 3.32±0.05, 3.22±0.05.

8. A crystalline form of astaxanthin designated crystal Form I having
    an X-ray diffraction pattern comprising the following interlattice plane interval d in $10^{-10}$ m: 8.0±0.1, 6.5±0.05, 6.3±0.05, 6.1±0.05, 5.96±0.05, 5.58±0.05, 5.43±0.05, 4.87±0.05, 4.32±0.05, 4.24±0.05, 4.21±0.05, 4.07±0.05, 4.03±0.05, 3.58±0.05, 3.50±0.05.

9. A crystalline form of astaxanthin designated crystal Form I providing an X-ray powder diffraction pattern substantially in agreement with the X-ray powder diffraction pattern provided in FIG. 1.

10. A crystalline form of astaxanthin designated crystal Form I according to claim 9, wherein the crystal Form I has a Raman spectrum substantially in agreement with the Raman spectrum provided in FIG. 2.

11. A crystalline form of astaxanthin designated crystal Form I according to claim 8 comprising all-trans-astaxanthin and at least about 13 mol % of at least one carotenoidal compound.

12. A crystalline form of astaxanthin designated crystal Form I according to claim 8 comprising all-trans-astaxanthin and at least 13 mol % of at least one carotenoidal compound, selected from the group consisting of 9-cis-astaxanthin, 13-cis-astaxanthin, 15-cis-astaxanthin, astacene, semi-astacene and C-25 aldehyde.

13. A crystalline form of astaxanthin designated crystal Form II having
an X-ray diffraction pattern comprising the following interlattice plane intervals d in $10^{-10}$ m: 7.2±0.1, 6.6±0.05, 6.5±0.05, 5.48±0.05, 5.34±0.05, 5.27±0.05, 4.49±0.05, 4.38±0.05, 4.12±0.05, 3.89±0.05, 3.61±0.05, 3.56±0.05, 3.34±0.05, 3.32±0.05, 3.22±0.05.

14. A crystalline form of astaxanthin designated crystal Form II providing an X-ray powder diffraction pattern substantially in agreement with the X-ray powder diffraction pattern provided in FIG. 3.

15. A crystalline form of astaxanthin designated crystal Form II according to claim 14, wherein the crystal form II has a Raman spectrum substantially in agreement with the Raman spectrum provided in FIG. 4.

16. A crystalline form of astaxanthin designated crystal Form II according to claim 13 comprising all-trans-astaxanthin and maximally 7 mol % of at least one carotenoidal compound.

17. A crystalline form of astaxanthin designated crystal Form II according to claim 13 comprising all-trans-astaxanthin and maximally 7 mol % of at least one carotenoidal compound, selected from the group consisting of at least one 9-cis-astaxanthin, 13-cis-astaxanthin, 15-cis-astaxanthin, astacene, semi-astacene and C-25 aldehyde.

18. A crystalline form of astaxanthin designated crystal Form II according to claim 13 wherein the astaxanthin: is in a solid form; forms a clear 0.05% solution in chloroform; has an absorption maximum wavelength of 484-493 nm in a solution of chloroform; has a residue on ignition of not more than 0.1%; contains a total carotenoid content other than astaxanthin of not more than 4%; contains lead of not more than 5 ppm; contains arsenic of not more than 2 ppm; contains mercury of not more than 1 ppm; and contains heavy metals of not more than 10 ppm.

19. An administration form of astaxanthin for the life science industry comprising crystal Form I or II of astaxanthin, or mixtures thereof according to claim 1.

20. An administration form of astaxanthin for fish feed, comprising crystal Form I or II of astaxanthin, or mixtures thereof according to claim 1 in which the content of astaxanthin is below 20% by weight.

21. An administration form of astaxanthin for fish feed, comprising a suspension of crystal Form I or II of astaxanthin, or mixtures thereof according to claim 1, wherein said administration form comprises an edible oil.

22. A process for preparing a mixture of crystalline forms of astaxanthin designated crystal Form I and crystal Form II according to claim 1 comprising at least 5 %w/w of Form I or Form II which comprises:
i) dissolving a mixture of astaxanthin that comprises all-trans-astaxanthin and 7 mol% to 17 mol% of at least one carotenoidal compound, selected from the group consisting of at least one 9-cis-astaxanthin, 1 3-cis-astaxanthin, 1 5-cis-astaxanthin, astacene, semi-astacene and C-25 aldehyde in a solvent selected from the group consisting of dichloromethane, trichloroethane, chloroform, dimethoxymethane, diethoxyethane, dioxacyclopentane, THF, NMP, N-ethylpyrrolidone, toluene, pyridine and carbon disulfide at a temperature up to the boiling point of said solvent and at least one of the following steps iia), iib) or iic),
iia) addition of an anti-solvent selected from the group consisting of methanol, ethanol, n-propanol, isopropanol, n-butanol, tert-butanol and water,
iib) removal of the solvent by evaporation, optionally by simultaneous exchange of the solvent with an anti solvent,
iic) cooling the organic solvent solution optionally with a nucleating agent or seed comprising crystal Form I or II, or mixtures thereof and
iii) harvesting, washing with an anti solvent and drying the crystals.

23. A process for preparing a crystalline form of astaxanthin designated crystal Form I, according to claim 8 which comprises:
i) dissolving a mixture of astaxanthin that comprises all-trans-astaxanthin and at least 13 mol% of at least one carotenoidal compound, selected from the group consisting of at least 9-cis-astaxanthin, 13-cis-astaxanthin, 15-cis-astaxanthin, astacene, semi-astacene and C-25 aldehyde dissolved in a solvent selected from the group consisting of dichloromethane, trichloroethane, chloroform, dimethoxymethane, diethoxyethane, dioxacyclopentane, THF, NMP, N-ethylpyrrolidone, toluene, pyridine and carbon disulfide at a temperature up to the boiling point of said solvent and at least one of the following steps iia), iib) or iic),
iia) addition of an anti-solvent selected from the group consisting of methanol, ethanol, n-propanol, isopropanol, n-butanol, tert-butanol and water,
iib) removal of the solvent by evaporation optionally by simultaneous exchange of the solvent with an anti solvent,
iic) cooling the organic solvent solution optionally with a nucleating agent or seed comprising crystal Form I and
iii) harvesting, washing with an anti solvent and drying the crystals.

24. A process for preparing crystalline form of astaxanthin designated crystal Form II according to claim 13 which comprises:
i) dissolving a mixture of astaxanthin that comprises all-trans-astaxanthin and maximally 7 mol% of at least one carotenoidal compound, selected from the group consisting of at least 9-cis-astaxanthin, 13-cis-astaxanthin, 15-cis-astaxanthin, astacene, semi-astacene and C-25 aldehyde in a solvent selected from the group consisting of dichloromethane, trichloroethane, chloroform, dimethoxymethane, diethoxyethane, dioxacyclopentane, THF, NMP, N-ethylpyrrolidone, toluene, pyridine and carbon disulfide at a temperature up to the boiling point of said solvent and at least one of the following steps iia), iib) or iic),
iia) addition of an anti-solvent selected from the group consisting of methanol, ethanol, n-propanol, isopropanol, n-butanol, tert-butanol and water,
iib) removal of the solvent by evaporation optionally by simultaneous exchange of the solvent with an anti solvent,
iic) cooling the organic solvent solution with the optional addition of a nucleating agent or seed comprising crystal Form II and iii) harvesting, washing with an anti solvent and drying the crystals.

25. A process which comprises further processing the mixture according to claim 1 to nutritional dosage forms.

26. A process for preparing the composition of claim 6 which comprises adding excipients to crystal Form I.

27. A process for preparing the composition of claim 7 which comprises adding excipients to crystal Form II.

28. A process to prepare an administration form of astaxanthin for fish feed or the life science industry wherein the mixture according to claim 1 is dissolved in an organic solvent or oil or mixtures thereof followed by further processing into said administration form.

29. A process to prepare an administration form of astaxanthin for the life science industry wherein the mixture according to claim 1 is dissolved in an organic solvent or oil or mixtures thereof followed by further processing into said administration form wherein said administration form comprises a lipophilic dispersant.

30. A process to prepare an administration form of astaxanthin for the life science industry wherein the mixture according to claim 1 is dissolved in an organic solvent or oil or mixtures thereof followed by further processing into said administration form wherein said administration form comprises a hydrophilic dispersant.

31. A process for preparing an oily composition comprising astaxanthin which method comprises dissolving the mixture according to claim 1 directly in an edible oil and/or fish oil at temperatures between 100° C. and 230° C. for direct incorporation in fish feed pellets.

32. The mixture according to claim 1, wherein the mixture is prepared by a process comprising:
   i) dissolving a mixture of astaxanthin that comprises all-trans-astaxanthin and 7 mol% to 17 mol% of at least one carotenoidal compound, selected from the group consisting of at least one 9-cis-astaxanthin, 13-cis-astaxanthin, 15-cis-astaxanthin, astacene, semi-astacene and C-25 aldehyde in a solvent selected from the group consisting of dichloromethane, trichloroethane, chloroform, dimethoxymethane, diethoxyethane, dioxacyclopentane, THF, NMP, N-ethylpyrrolidone, toluene, pyridine and carbon disulfide at a temperature up to the boiling point of said solvent and at least one of the following steps iia), iib) or iic),
   iia) addition of an anti-solvent selected from the group consisting of methanol, ethanol, n-propanol, isopropanol, n-butanol, tert-butanol and water,
   iib) removal of the solvent by evaporation, optionally by simultaneous exchange of the solvent with an anti solvent,
   iic) cooling the organic solvent solution optionally with a nucleating agent or seed comprising crystal Form I or II, or mixtures thereof and
   iii) harvesting, washing with an anti solvent and drying the crystals.

33. The mixture of claim 1, wherein the Crystal Form I has at least one of the following characteristics:
   a) a Raman spectrum containing peaks at 372±2, 346±2, 333±2, 312±2, 289±2, 234±2, 193±2, 178±2, 133±2, 82±2, cm$^{-1}$;
   b) a DSC scan showing a phase transition at 212-222° C.;
   c) a solubility profile in dichloromethane of 35-45 g/l at 20° C.-25° C.; and wherein the Crystal Form II has at least one of the following characteristics:
   aa) a Raman spectrum containing peaks at 376±2, 337±2, 314±2, 304±2, 289±2, 206±2, 180±2, 137±2, 107±2, 93±2, cm$^{-1}$;
   bb) a DSC scan showing a phase transition at 225-240° C.;
   cc) a solubility profile in dichloromethane of 10-30 g/l at 20° C.-25° C.

34. The mixture of claim 33, wherein the Crystal Form I has each of the characteristics a), b) and c), and the Crystal Form II has each of the characteristics aa), bb) and cc).

35. The composition of claim 6, wherein the crystal Form I has at least one of the following characteristics:
   a) a Raman spectrum containing peaks at 372±2, 346±2, 333±2, 312±2, 289±2, 234±2, 193±2, 178±2, 133±2, 82±2, cm$^{-1}$;
   b) a DSC scan showing a phase transition at 212-222° C.;
   c) a solubility profile in dichloromethane of 35-45 g/l at 20° C.-25° C.

36. The composition of claim 35, wherein the crystal Form I has each of the characteristics a), b) and c).

37. The composition of claim 7, wherein the crystal Form II has at least one of the following characteristics:
   aa) a Raman spectrum containing peaks at 376±2, 337±2, 314±2, 304±2, 289±2, 206±2, 180±2, 137±2, 107±2, 93±2, cm$^{-1}$;
   bb) a DSC scan showing a phase transition at 225-240° C.;
   cc) a solubility profile in dichloromethane of 10-30 g/l at 20° C.-25° C.

38. The composition of claim 37, wherein the crystal Form II has each of the characteristics aa), bb) and cc).

39. The crystalline form of astaxanthin of claim 8, wherein the crystal Form I has at least one of the following characteristics:
   a) a Raman spectrum containing peaks at 372±2, 346±2, 333±2, 312±2, 289±2, 234±2, 193±2, 178±2, 133±2, 82±2, cm$^{-1}$;
   b) a DSC scan showing a phase transition at 212-222° C.;
   c) a solubility profile in dichloromethane of 35-45 g/l at 20° C.-25° C.

40. The crystalline form of astaxanthin of claim 39, wherein the crystal Form I has each of the characteristics a), b) and c).

41. The crystalline form of astaxanthin of claim 13, wherein the crystal Form II has at least one of the following characteristics:
   aa) a Raman spectrum containing peaks at 376±2, 337±2, 314±2, 304±2, 289±2, 206±2, 180±2, 137±2, 107±2, 93±2, cm$^{-1}$;
   bb) a DSC scan showing a phase transition at 225-240° C.;
   cc) a solubility profile in dichloromethane of 10-30 g/l at 20° C.-25° C.

42. The crystalline form of astaxanthin of claim 41, wherein the crystal Form II has each of the characteristics aa), bb) and cc).

* * * * *